US012758332B2

(12) United States Patent
Dachs, II et al.

(10) Patent No.: US 12,758,332 B2
(45) Date of Patent: Oct. 13, 2026

(54) INSTRUMENT ADAPTOR, AND RELATED DEVICES, SYSTEMS AND METHODS

(71) Applicant: INTUITIVE SURGICAL OPERATIONS, INC., Sunnyvale, CA (US)

(72) Inventors: Gregory W. Dachs, II, San Mateo, CA (US); Gabriel F. Brisson, Livermore, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 84 days.

(21) Appl. No.: 18/851,325

(22) PCT Filed: Mar. 17, 2023

(86) PCT No.: PCT/US2023/015434
§ 371 (c)(1),
(2) Date: Sep. 26, 2024

(87) PCT Pub. No.: WO2023/192034
PCT Pub. Date: Oct. 5, 2023

(65) Prior Publication Data

US 2025/0221779 A1 Jul. 10, 2025

Related U.S. Application Data

(60) Provisional application No. 63/325,371, filed on Mar. 30, 2022.

(51) Int. Cl.

| | |
|---|---|
| ***A61B 34/30*** | (2016.01) |
| ***A61B 46/10*** | (2016.01) |
| ***B25J 15/04*** | (2006.01) |

(52) U.S. Cl.
CPC .............. *A61B 34/30* (2016.02); *A61B 46/10* (2016.02); *B25J 15/0408* (2013.01)

(58) Field of Classification Search
None
See application file for complete search history.

(56) References Cited

U.S. PATENT DOCUMENTS

2008/0140088 A1* 6/2008 Orban, III .............. A61B 46/10 606/130
2021/0093398 A1* 4/2021 Ago ........................ A61B 34/30

FOREIGN PATENT DOCUMENTS

EP 3714830 A1 9/2020
WO WO-2009061915 A2 5/2009

(Continued)

OTHER PUBLICATIONS

International Search Report and Written Opinion for Application No. PCT/US2023/015434, mailed Jun. 28, 2023, 10 pages.

(Continued)

*Primary Examiner* — Mallika D Fairchild
(74) *Attorney, Agent, or Firm* — Jones Burke, PLLC

(57) ABSTRACT

An adaptor for operatively coupling a drive output of a drive output interface to a drive input of an instrument comprises a frame and a coupler coupled to the frame. The frame comprises a first face configured to mount to the drive output interface and a second face configured to receive the instrument mounted thereon. The coupler comprises one or more first engagement features configured to engage with the drive output and one or more second engagement features configured to engage with the drive input. The coupler also comprises one or more compliance features configured to allow a first input engagement feature of the input engagement features to move towards the instrument in a state in which the coupler is engaged with the drive output and a (Continued)

second input engagement feature of the input engagement features is in contact with a coupler facing surface of the drive input.

20 Claims, 18 Drawing Sheets

(56) References Cited

FOREIGN PATENT DOCUMENTS

| | | | |
|---|---|---|---|
| WO | WO-2015023840 | A1 | 2/2015 |
| WO | WO-2015142789 | A1 | 9/2015 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

INSTRUMENT ADAPTOR, AND RELATED DEVICES, SYSTEMS AND METHODS

CROSS-REFERENCE TO RELATED APPLICATION

This application is a U.S. national stage application under 35 U.S.C. § 371 (c) of International PCT Application No. PCT/US2023/015434, filed Mar. 17, 2023, which claims the benefit of priority to U.S. Provisional Application No. 63/325,371, filed Mar. 30, 2022 and titled "INSTRUMENT ADAPTOR, AND RELATED DEVICES, SYSTEMS AND METHODS" the entire contents of each of which are incorporated by reference herein.

FIELD

Aspects of this disclosure relate generally to instrument adaptors for use with remotely controllable instruments, and related devices, systems, and methods. In particular, aspects of the disclosure relate to instrument sterile adaptors, and related device, systems, and methods, for use in in procedures performed in a sterile environment, such as medical procedures.

INTRODUCTION

Remotely controllable instruments, such as for use in medical procedures, industrial procedures, or other procedures, generally comprise an end effector at one end portion of a shaft and a force transmission assembly at an opposite end portion of the shaft. The end effector performs one or more functions (e.g., grasping, cutting, imaging etc.) and is coupled by actuation elements to one or more drive inputs of the force transmission assembly. The drive inputs receive driving forces or other inputs (e.g., electricity, etc.) to control degrees of freedom of motion and/or functions of the instrument. In some systems, the driving forces or other inputs are supplied to the drive inputs of the force transmission assembly by a drive output interface to which the instrument is coupled. For example, the drive output interface may be part of a manipulator of a computer-assisted teleoperated system to which the instrument is removably couplable, with the interface comprising one or more drive outputs to supply the driving forces or other inputs. Such computer-assisted teleoperated systems may comprise one or more such manipulators, which may support, move, and/or provide forces to manipulate instruments coupled thereto, and the manipulators along with their corresponding drive outputs may be operated, for example, under the remote control of an operator at a console having user-manipulated input devices.

In some arrangements, an instrument adaptor may be interposed between the instrument and the drive output interface that supplies the driving forces. For example, the instrument adaptor may comprise couplers that couple drive outputs of the interface positioned on one side of the adaptor to drive inputs of the instrument positioned on the other side of the adaptor. The couplers of the adaptor mechanically transfer driving forces/motion of the drive outputs to the drive inputs. The instrument adaptor may also comprise attachment features that facilitate attachment or mounting of the instrument to the interface, with the adaptor being directly mounted to the interface and the instrument in turn mounted to the adaptor.

Various medical procedures, such as surgical, diagnostic, therapeutic, or imaging procedures, may require a sterile field in an environment including and within a distance around a patient. Some industrial procedures, for example manufacturing of sensitive electronic components, also may require or benefit from establishing a sterile field. A sterile field is a region in which any exposed surfaces of objects in the region are maintained in a sterile condition (i.e., a condition substantially free from one or more contaminants, such as biological pathogens, dusts, oils, etc.). Sterile barrier devices, such as sterile drapes and the like, may help to establish such a sterile field by covering non-sterile surfaces and exposing a sterile surface of the sterile barrier device to the environment of the sterile field instead of the now-covered surface of the object. In this way, the lack of sterility of the covered surface of the object does not compromise the sterility of the sterile field.

In addition to coupling an instrument to an interface, an instrument adaptor may be configured to provide a sterile barrier between the instrument and the interface to which the instrument is coupled. In such cases, the instrument adaptor may be referred to as an instrument sterile adaptor ("ISA"). The ISA may be used in conjunction with other sterile barrier devices, such as a sterile drape, to establish a sterile field in or around at least part of an environment or worksite. For example, in some cases an ISA and a sterile drape may be coupled together to form a sterile drape assembly that collectively creates a sterile barrier around portions of equipment (e.g., a manipulator of a computer-assisted teleoperated system), including an interface of the equipment to which an instrument may be coupled. In such examples, the ISA is interposed between the interface of the equipment and an instrument mounted thereto, and the sterile drape coupled to the ISA is used to cover remaining portions of the equipment (e.g., a manipulator arm). A benefit of using the ISA at the region where the instrument and the interface are coupled together is that the ISA may be designed to facilitate force and motion transfer between the drive outputs of the manipulator interface and drive inputs of the force transmission assembly of the instrument while still maintaining a sterile barrier, whereas sterile drapes or other barrier devices may not always be suitable for such use, as the drape may interfere with the engagement between drive outputs and drive inputs, interfere with motion of the drive outputs/drive inputs, and/or be damaged by the motion of the drive outputs.

When an instrument adaptor (whether sterile or not) is used to couple an instrument to a drive output interface, it is important that each coupler of the adaptor positively engage with the corresponding drive output of the interface and the corresponding drive input of the instrument so that the above-described transfer of forces/motion can occur. Specifically, each coupler of the adaptor comprises engagement features (such as male and/or female features) that are configured to mate with corresponding complementary engagement features (complementary female and/or male features, respectively) of the drive outputs and the drive inputs. When so engaged, the engagement features and complementary engagement features mechanically couple the drive output, coupler, and drive input together such that they are constrained to move together and thereby transfer driving forces/motion from the drive output to the drive input. For the engagement features of the coupler to successfully engage with the complementary engagement features of the drive outputs/inputs, the engagement and complementary engagement features generally need to be aligned with one another. However, such alignment might not occur initially during the mounting/installation of the adaptor and/or instrument. To address this issue, some systems are configured to perform a coupling procedure after mounting of the ISA and/or instrument in an attempt to bring about the alignment of the engagement and complementary engagement features. For example, the coupling procedure may comprise actuating the drive outputs of the drive output interface in a predetermined manner while urging the coupler and drive outputs/inputs together until the engagement and complementary features are brought into alignment. However, positive engagement between an adaptor coupler and its corresponding drive output or drive input may prove difficult, notwithstanding the performance of the coupling procedure. Accordingly, a need exists to improve the ability of couplers of instrument adaptors to achieve positive engagement with drive outputs and/or drive inputs.

SUMMARY

Various embodiments of the present disclosure may solve one or more of the above-mentioned problems and/or may demonstrate one or more of the above-mentioned desirable features. Other features and/or advantages may become apparent from the description that follows.

In accordance with at least one embodiment of the present disclosure, an adaptor for operatively coupling a drive output of a drive output interface to a drive input of an instrument comprises a frame and a coupler coupled to the frame. The frame comprises a first face configured to mount to the drive output interface and a second face configured to receive the instrument mounted thereon. The coupler comprises one or more output engagement features configured to engage with the drive output in a mounted state of the frame to the drive output interface. The coupler also comprises one or more input engagement features configured to engage with the drive input in a mounted state of the instrument to the frame. The coupler also comprises one or more compliance features configured to allow a first input engagement feature of the input engagement features to move towards the instrument in a state in which the coupler is engaged with the drive output and a second input engagement feature of the input engagement features is in contact with a coupler facing surface of the drive input. In some embodiments, the compliance features comprise tilt features configured to contact the drive output such that the coupler is tiltable about a tilt axis defined by the tilt features in an engaged state of the coupler with the drive output. In some embodiments, the compliance features comprise a flexible support member coupling the second input engagement feature to a remainder of the coupler such that the second input engagement feature is movable relative to a remainder of the coupler via flexing of the flexible support member.

In accordance with at least one embodiment of the present disclosure, an adaptor for operatively coupling a drive output of a drive output interface to a drive input of an instrument comprises a frame and a coupler coupled to the frame. The frame comprises a first face configured to mount to the drive output interface and a second face configured to receive the instrument mounted thereon. The coupler comprises one or more first engagement features configured to engage with the drive output in a mounted state of the frame to the drive output interface. The coupler also comprises one or more second engagement features configured to engage with the drive input in a mounted state of the instrument to the frame. The coupler also comprises one or more compliance features configured to, in an engaged state of the coupler with the drive output, allow an engagement axis that is tangent to the second engagement features to tilt relative to the drive input in response to contact by a coupler facing surface of the drive input with one of the second engagement features. In some embodiments, the compliance features comprise tilt features. In some embodiments, the compliance features comprise a flexible support member.

In accordance with at least one embodiment of the present disclosure, an adaptor for operatively coupling a drive output of a drive output interface to a drive input of an instrument comprises a frame and a coupler coupled to the frame. The frame comprises a first face configured to mount to the drive output interface and a second face configured to receive the instrument mounted thereon. The coupler comprises one or more first engagement features configured to engage with the drive output in a mounted state of the frame to the drive output interface. The coupler also comprises one or more second engagement features configured to engage with the drive input in a mounted state of the instrument to the frame. The coupler also comprises one or more tilt features configured to contact the drive output such that the coupler is tiltable about a tilt axis defined by the tilt features in an engaged state of the coupler with the drive output.

In accordance with another embodiment of the present disclosure, an adaptor comprises a frame and a coupler movably coupled to the frame. The frame comprises a first face configured to mount to a drive output interface and a second face configured to receive an instrument mounted thereon. The coupler is configured to couple a drive output of the drive output interface to a drive input of the instrument and is rotatable about a first axis. In a state of the coupler engaged with a drive output of the drive output interface, the coupler is tiltable relative to the drive output about a second axis that is perpendicular to the first axis.

In accordance with yet another embodiment of the present disclosure, a sterile drape assembly comprises an instrument sterile adaptor and a drape coupled to the instrument sterile adaptor. The instrument sterile adaptor comprises a frame and a coupler movably coupled to the frame. The frame comprises a first face configured to mount to a drive output interface of equipment and a second face configured to receive an instrument mounted thereon. The drape is coupled to the frame and configured to cover a portion of the equipment. The coupler comprises one or more first engagement features configured to engage with a drive output of the drive output interface in a mounted state of the frame to the drive output interface. The coupler also comprises one or more second engagement features configured to engage with a drive input of the instrument in a mounted state of the instrument to the frame. The coupler also comprises one or more tilt features configured to contact the drive output such that the coupler is tiltable about a tilt axis defined by the tilt features in an engaged state of the coupler with the drive output.

In accordance with another embodiment of the present disclosure, a method of using an adaptor to couple a drive output interface to an instrument comprises mounting an adaptor to a drive output interface, engaging a coupler of the adaptor with a drive output of the drive output interface, mounting an instrument to the adaptor, and engaging the coupler with a drive input of the instrument by causing the coupler to tilt relative to the drive output while rotating the coupler.

In accordance with yet another embodiment of the present disclosure, a method of coupling an instrument to an adaptor, which is coupled to a drive output interface, comprises, in an engaged state of a coupler of the adaptor with a drive output of the drive output interface, engaging second engagement features of the coupler with a drive input of the instrument by: rotating the coupler and causing the coupler to tilt relative to the drive output and while rotating the coupler.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 3:
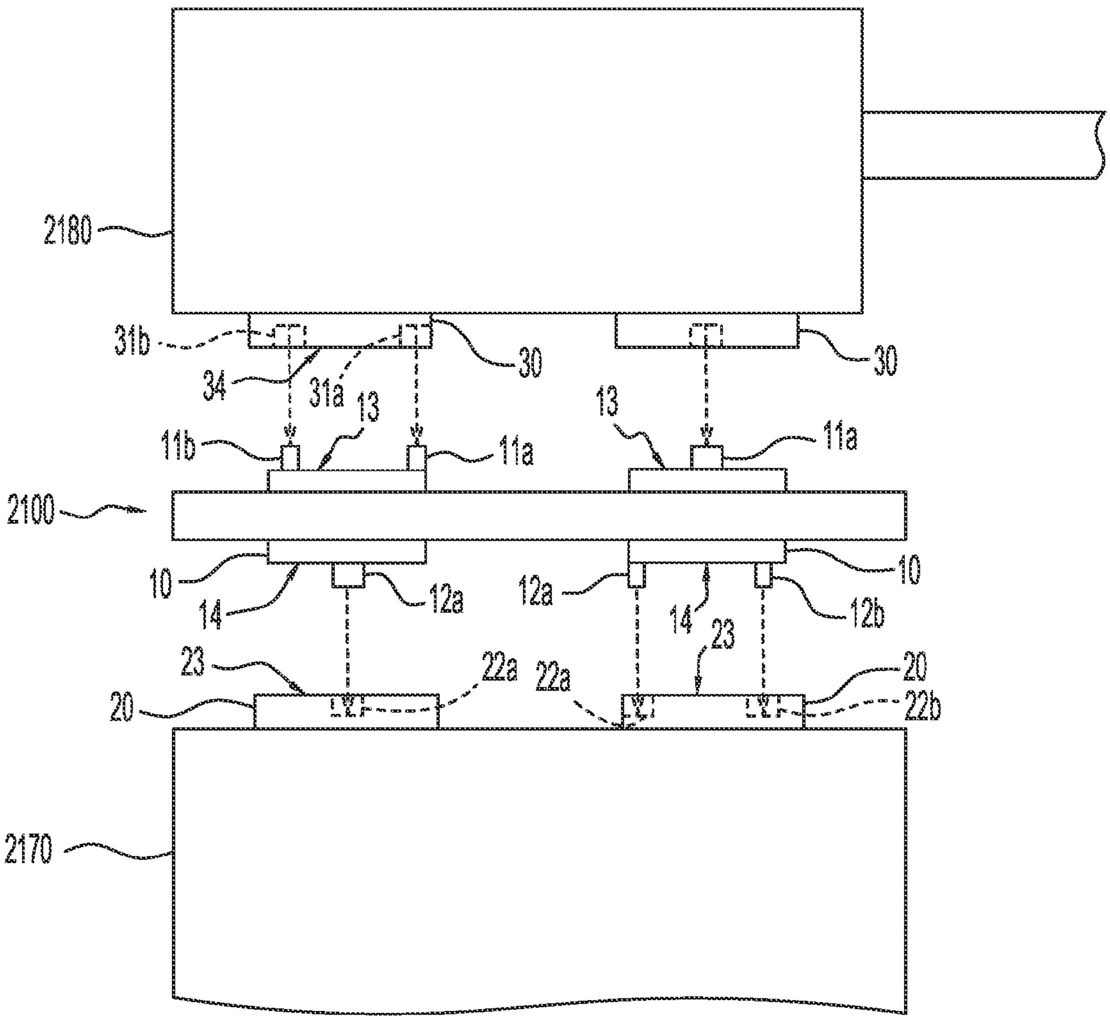
FIG. 3 is a schematic, exploded side view of an embodiment of an instrument adaptor comprising the adaptor coupler of FIG. 1A in a mounted state of the instrument adaptor on an interface and a mounted state of an instrument on the instrument adaptor.
Figure 16:
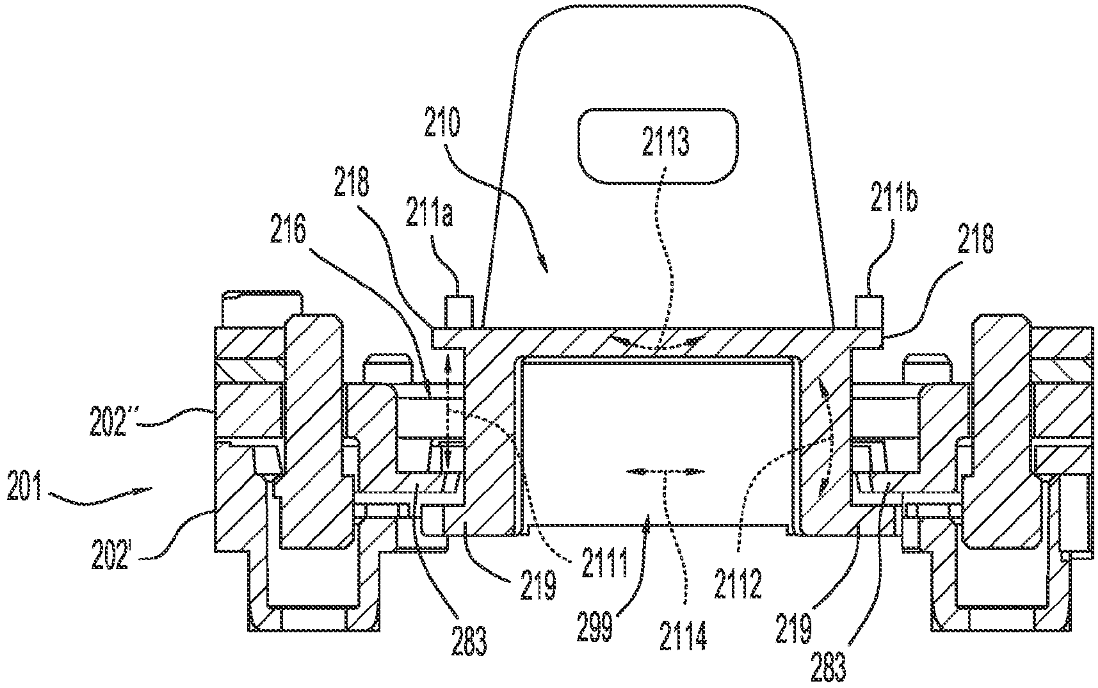
FIG. 16 is cross-section of the instrument adaptor of FIG. 9 with the section taken along 16-16 in FIG. 15.

As noted above, positive engagement between a coupler of an instrument adaptor and a drive output or drive input can be problematic to achieve reliably and efficiently. An example embodiment of such an adaptor is illustrated in FIG. 3, which comprises a schematic exploded side view of an embodiment of an adaptor 2100. As shown in FIG. 16, the adaptor 2100 may be interposed between a drive output interface 2170 (e.g., of a manipulator) and an instrument 2180. The adaptor 2100 comprises one or more adaptor couplers 10, each to couple with a corresponding drive output 20 of the drive output interface 2170 and a corresponding drive input 30 of the instrument 2180. The drive outputs 20, adaptor couplers 10, and drive inputs 30 are configured to transfer driving forces via rotation, and they comprise complementary engagement features that engage (mate) with one another to constrain their relative rotation. In particular, as shown in FIG. 3, the adaptor coupler 10 comprises engagement features 12*a* and 12*b* disposed on a drive output engaging surface 14 of the adaptor coupler 10 that are to engage (mate) with respectively corresponding complementary engagement features 22*a* and 22*b* disposed on an adaptor engaging surface 23 of the drive output 20, as well as engagement features 11*a* and 11*b* disposed on an input engaging surface 13 of the adaptor coupler that are to engage (mate) with respectively corresponding complementary engagement features 31*a* and 31*b* disposed on an adaptor engagement surface 34 of the drive input 30. The engagement features 12*a* and 12*b* may also be referred to herein as "output engagement features," and the engagement features 11*a* and 11*b* may also be referred to herein as "input engagement features." The engagement features 12*a* and 12*b* and the engagement features 11*a* and 11*b* may also be referred to arbitrarily using the labels "first" or "second" (e.g., "first engagement features"). When all of the aforementioned engagement features are in mating engagement, rotation of the drive output 20 drives rotation of the adaptor coupler 10 which in turn drives rotation of the drive input 30 of the instrument 2180. The rotation of the drive outputs 20 may be driven by actuators, such as servo motors, contained within or coupled to the drive output interface 2170. The rotation of the drive inputs 30 may control one or more degrees of freedom of motion or other functions of the instrument 2180, such as driving motion of or actuating a function of an end effector (not illustrated) of the instrument. In the illustrated embodiment, the engagement features 11*a*, 11*b*, 12*a*, 12*b* of the adaptor coupler are all protrusions and the complementary engagement features 22*a*, 22*b*, 31*a*, 31*b* are all recess configured to receive the protrusions when in mating engagement. Those having ordinary skill in the art would appreciate that the various engagement features and their respectively corresponding complementary engagement features could comprise any other combinations of recesses and protrusions in other embodiments.

Figure 1A:
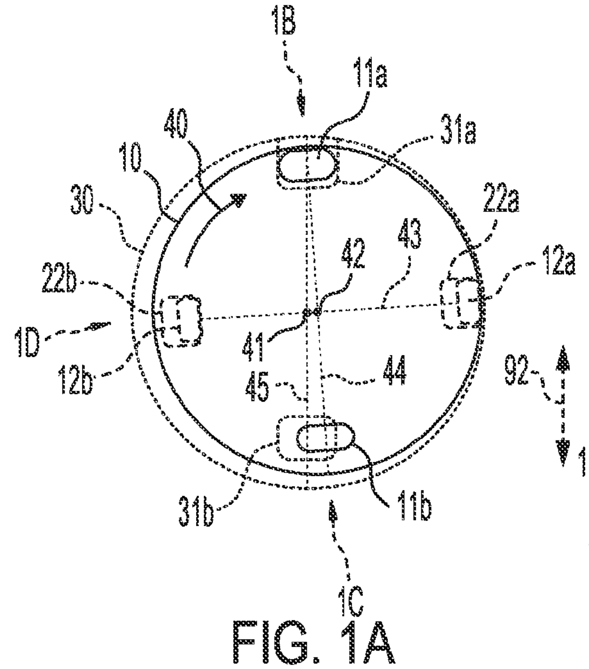
FIG. 1A is a schematic plan view of an embodiment of an adaptor coupler coupled to a drive output and in a first state while attempting to engage with a drive input, from the perspective 1A in FIG. 1B.

Turning now to FIGS. 1A-2D, an engagement sequence that can occur which may lead to a lack of positive engagement of an adaptor coupler with a drive output or input is schematically illustrated and described below. FIGS. 1A and 2A are plan views looking down from a perspective above an embodiment of an adaptor coupler 10 of the adaptor 2100 of FIG. 3, as indicated by arrows 1A and 2A, respectively, in FIGS. 1B and 2B. FIGS. 1B-1D and 2B-2D are side views from perspectives indicated by arrows 1B-1D and 2B-2D in FIGS. 1A and 2A. In FIGS. 1A and 2A, the drive input 30 is made transparent and indicated by dashed lines. In FIGS. 1A and 2A, for the purposes of clarity, the drive output 20 is not illustrated except for the complementary engagement features 22*a* and 22*b* thereof which are indicated by dashed lines.

In the situation illustrated in FIGS. 1A-2D it is assumed that the instrument adaptor 2100 (not illustrated in FIGS. 1A-2D) has already been mounted to the drive output interface 2170 (not illustrated in FIGS. 1A-2D) and an adaptor coupler 10 of the adaptor is already positively engaged with a drive output 20 of the drive output interface, meaning that the engagement features 12*a* and 12*b* are in mating engagement with the respectively corresponding complementary engagement features 22*a* and 22*b*, as illustrated in FIGS. 1A-1D. Thereafter, when the instrument 2180 (not illustrated in FIGS. 1A-2D) is mounted to the adaptor (see FIG. 3), the engagement features 11*a* and 11*b* are not initially aligned with the respectively corresponding complementary engagement features 31*a* and 31*b*. In an attempt to bring the engagement features 11*a* and 11*b* and complementary engagement features 31*a* and 31*b* into alignment with one another so as to cause positive mating engagement, the adaptor coupler 10 may be rotated by driving the drive output 20 of the drive output interface 2170 to rotate. One or both of the adaptor coupler 10 and the drive input 30 may be urged toward the other during this process, for example by a biasing device such as a spring that applies a biasing force, so that the drive input 30 and/or adaptor coupler 10 are moved toward one another when the engagement features 11*a* and 11*b* and complementary engagement features 31*a* and 31*b* are eventually brought into alignment, resulting in the engagement features 11*a* and 11*b* being brought into mating engagement with (e.g., received in) the complementary engagement features 31*a* and 31*b*. Prior to the aforementioned alignment of the engagement features with the complementary engagement features, the engagement features 11*a* and 11*b* of the adaptor coupler 10 and the surface of the drive input 30 are pressed against one another by the biasing force, with the engagement features 11*a* and 11*b* sliding along the bottom surface of the drive input 30 as the adaptor coupler 10 is rotated.

Figure 1B:
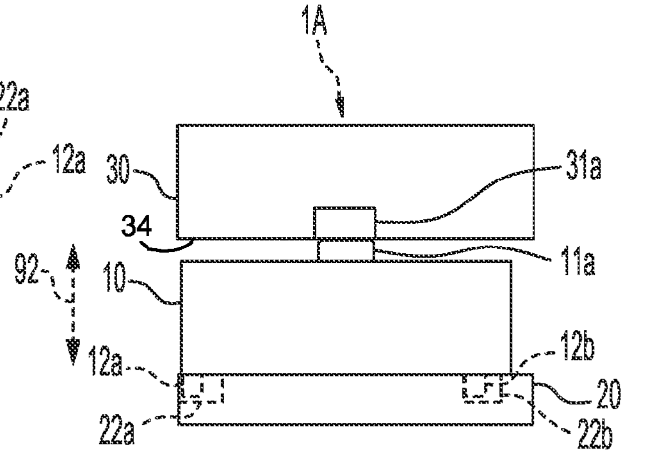
FIG. 1B is a first schematic side view of the adaptor coupler of FIG. 1A in the first state from the perspective 1B in FIG. 1A.
Figure 1C:
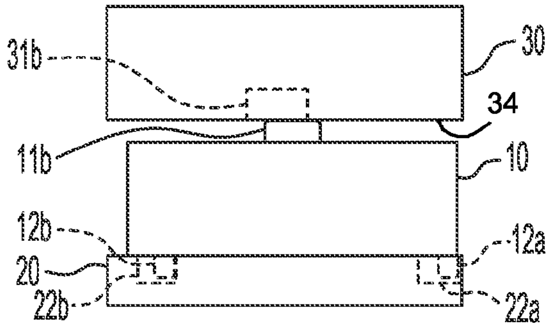
FIG. 1C is a second schematic side view of the adaptor coupler of FIG. 1A in the first state from the perspective 1C in FIG. 1A.
Figure 1D:
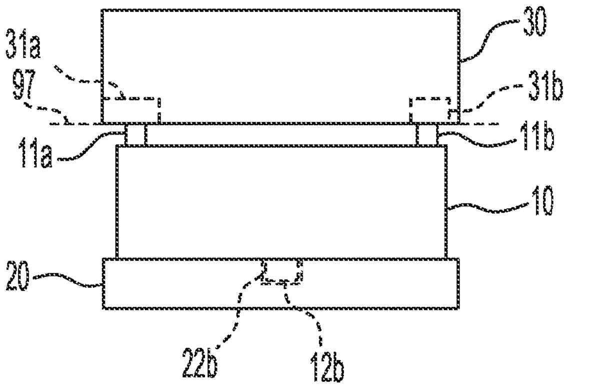
FIG. 1D is a third schematic side view of the adaptor coupler of FIG. 1A in the first state from the perspective 1D in FIG. 1A.
Figure 2A:
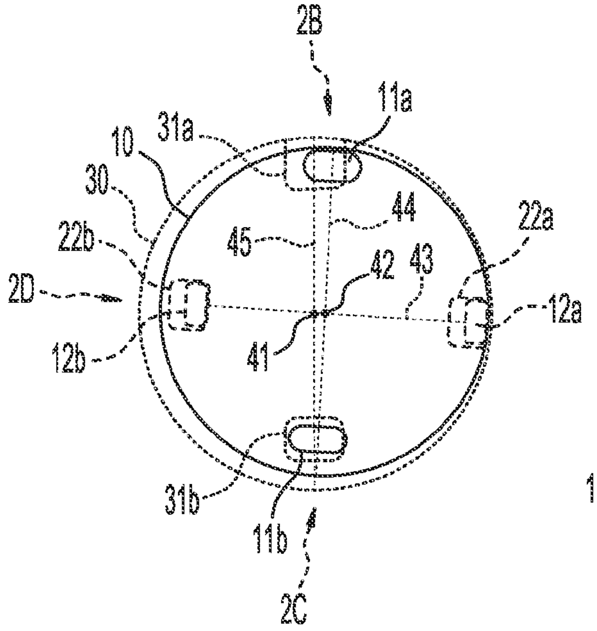
FIG. 2A is a schematic plan view of the adaptor of FIG. 1A in a second state while attempting to engage with the drive input, from the perspective 2A in FIG. 2B.
Figure 2B:
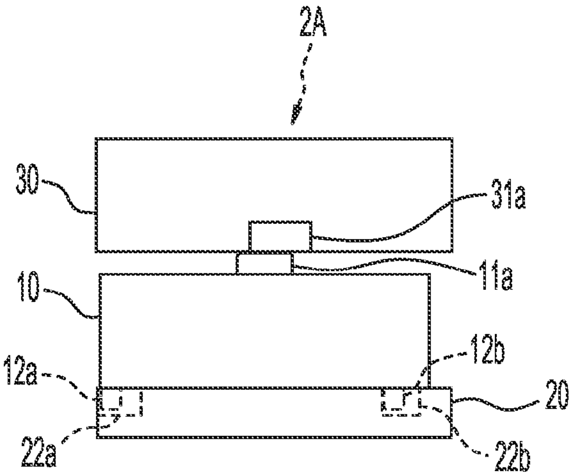
FIG. 2B is a first schematic side view of the adaptor coupler of FIG. 2A in the second state from the perspective 2B in FIG. 2A.
Figure 2C:
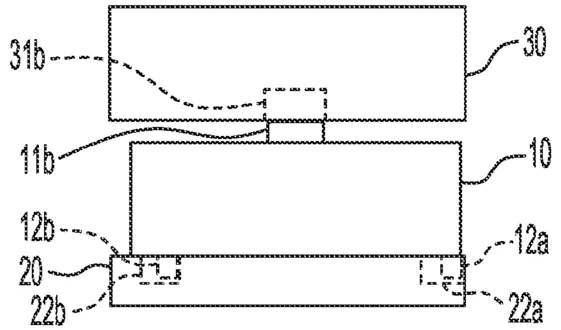
FIG. 2C is a second schematic side view of the adaptor coupler of FIG. 2A in the second state from the perspective 2C in FIG. 2A.
Figure 2D:
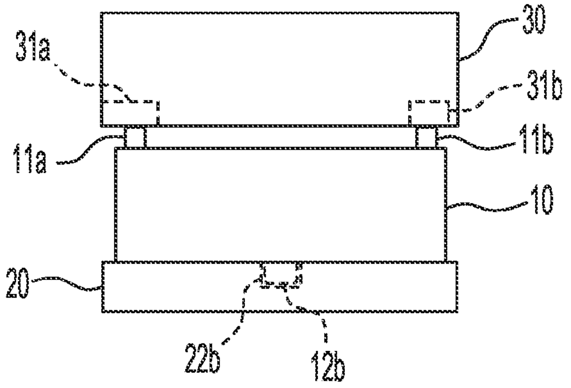
FIG. 2D is a third schematic side view of the adaptor coupler of FIG. 2A in the second state from the perspective 2D in FIG. 2A.

However, in the engagement sequence described above, in some circumstances, the adaptor coupler 10 and the drive input 30 are not aligned with one another during an attempted engagement of the engagement features and complementary engagement features. In particular, in the situation depicted in FIG. 1A, the center point 42 of the adaptor coupler 10 (corresponding to the axis of rotation thereof) is shifted relative to the center point 41 of the drive input 30 (corresponding to the axis of rotation thereof), causing the adaptor coupler and drive input to be misaligned (e.g., skewed with respect to the alignment of each of the individual engagement and complementary engagement features as shown). This lack of alignment between adaptor coupler 10 and drive input 30 may occur because the adaptor coupler 10 maintains some freedom of motion even after being coupled with the drive output 20. For example, in some systems the complementary engagement features 22*a* and 22*b* are wider than the engagement features 12*a* and 12*b* along one dimension, which allows the adaptor coupler 10 to move to some extent along an axis 43 parallel to the width dimension (and generally parallel to the interfaces of the adaptor coupler instrument engaging face and manipulator interface engaging face) even while the engagement features 12*a* and 12*b* are in mating engagement with the complementary engagement features 22*a* and 22*b*. (Note that the axis 43 is fixed relative to the adaptor coupler 10 and the drive output 20 once they are engaged, and thus the axis 43 will rotate relative to the drive input 30 as the adaptor coupler 10 and drive output 20 rotate relative to the drive input 30. In addition, although the axis 43 may intersect the center point 41 of the drive input 30 at some orientations of the adaptor coupler 10 as the adaptor coupler 10 rotates relative to the drive input 30, the axis 43 does not always intersect the center point 41 at other orientations of the adaptor coupler 10, unless the center points 42 and 41 happen to be aligned.) This degree of freedom of motion along the axis 43 may be intentionally built into the system to allow the coupler 10 to rotatably couple the drive output 20 and the drive input 30 together despite not being precisely aligned with one another, in a manner similar to how an Oldham coupling works. But this degree of freedom of motion also can result in the adaptor coupler 10 not being aligned with the drive input 30 during the mounting process, which can interfere with the engagement sequence. This misalignment could occur even if the parts are exactly perfect in their dimensions, due to motion of the adaptor coupler 10 along the above-described degree of freedom of motion. Moreover, real world manufacturing tolerances in the parts may also cause (or contribute to) misalignment in addition to or in lieu of the above-described degree of freedom of motion. Regardless of how the misalignment occurs, if the adaptor coupler 10 is not aligned with the drive input 30, then when the adaptor coupler 10 is rotated in an attempt to bring the engagement features 11*a* and 11*b* into alignment with the complementary engagement features 31*a* and 31*b* of the instrument, the engagement features 11*a* and 11*b* may not come into alignment with their corresponding complementary engagement features 31*a* and 31*b* at the same time as one another. Instead, one of the engagement features 11*a* and 11*b* may come into alignment with one of the complementary engagement features 31*a* and 31*b* while the other of the engagement features 11*a* and 11*b* remains out of alignment with the other of the complementary engagement features 31*a* and 31*b*. For example, if the adaptor coupler 10 is rotated in the direction indicated by the arrow 40, it can be seen that in the state in which the engagement feature 11*a* comes into alignment with the engagement feature 31*a*, the other engagement feature 11*b* is out of alignment with the engagement feature 31*b*, as illustrated in FIGS. 1A-1C. Similarly, in the state in which the second engagement feature 11*b* comes into alignment with the engagement feature 31*b*, the engagement feature 11*a* is out of alignment with the engagement feature 31*a*, as illustrated in FIGS. 2A-2C. Although the engagement features 11*a* and 31*a* are aligned with one another in the state illustrated in FIGS. 1A-1D, the engagement feature 11*a* cannot come into mating engagement with (e.g., be received in) the engagement feature 31*a* because in this state the engagement feature 11*b* is out of alignment with the engagement feature 31*b*. Because of the misalignment, the engagement feature 11*b* contacts the surface of the drive input 30, as shown in FIG. 1C, and this prevents the engagement feature 11*a* and the engagement feature 31*a* from moving toward one another. More specifically, in the state illustrated in FIG. 1A-1D, the adaptor coupler 10 and drive input 30 are highly constrained and consequently in this state neither the adaptor coupler 10 nor the drive input 30 can change their respective orientations (their freedom of motion being limited essentially to rotation, movement towards one another along direction 92, and limited translation of the adaptor coupler along axes 43 and 45). Thus, because the orientation of the adaptor coupler 10 and the drive input 30 cannot change, when the engagement feature 11*b* contacts the drive input 30, this stops substantially all motion of the adaptor coupler 10 and the drive input 30 toward one another along the direction 92 and consequently the engagement features 11*a* cannot move into the complementary engagement feature 31*a* despite being aligned. After the state described above, the adaptor coupler 10 will continue to rotate in the direction 40 and eventually the second engagement feature 11*b* will come into alignment with the engagement feature 31*b*, as shown in FIG. 2A. However, at this point the first engagement feature 11*a* has already moved out of alignment with the engagement feature 31*a*, as shown in FIGS. 2A and 2B. Thus, the engagement feature 11*a* now contacts the bottom of the drive input 30 and prevents the adaptor coupler 10 and the drive input 30 from moving toward one another, thus preventing the second engagement feature 11*b* from engaging with the engagement feature 31*b*. Thus, to summarize, because the adaptor coupler 10 is misaligned relative to the drive input 30, each time that one of the engagement features 11*a* or 11*b* comes into alignment with its corresponding engagement feature 31*a* or 31*b*, the other one of the engagement features 11*b* or 11*a* is out of alignment with its corresponding engagement feature 31*b* or 31*a* and thus prevents the engagement feature 11*a* or 11*b* from achieving positive mating engagement.

Positive engagement of the engagement features 11*b* and 11*a* with the corresponding engagement features 31*b* and 31*a* can also be prevented by other conditions besides misalignment of the adaptor coupler 10 and drive input 30. For example, if the adaptor coupler 10 and the drive input 30 are not parallel to one another, this might prevent positive engagement. The adaptor coupler 10 could be non-parallel to the drive input 30 because, for example, the instrument is mounted to the adaptor at an orientation that is slightly skewed from the nominally correct orientation. Due to the adaptor coupler 10 not being parallel to the drive input 30, when the engagement features 11*b* and 11*a* become aligned with the engagement features 31*b* and 31*a* it is possible that one of the engagement features 11*a* or 11*b* will engage with its corresponding engagement feature 31*a* or 31*b* but that the other engagement feature 11*b* or 11*a* will miss its corresponding engagement feature 31*b* or 31*a*. This can occur because the corresponding engagement feature 31*b* or 31*a* is vertically spaced from (e.g., positioned too high above) the engagement feature 11*b* or 11*a*.

To address these and other challenges, various embodiments disclosed herein provide an adaptor that has one or more compliance features configured to allow a first input engagement feature to move toward the drive input (e.g., toward the instrument) in a state in which the coupler is engaged with the drive output and a second input engagement feature is in contact with a coupler facing surface of the drive input. In other words, the compliance features are configured to allow an engagement axis that is tangent to the free ends of the input engagement features to tilt relative to the drive input in response to contact by the coupler facing surface of the drive input with one of the input engagement features. In some embodiments, a compliance feature comprises a tilt feature and the tilting of the engagement axis is caused by tilting of the entire coupler about the tilt feature relative to the drive output and/or drive input. In other embodiments, a compliance feature comprises a flexible support member that carries the second input engagement feature and the tilting of the engagement axis is caused by flexing of the flexible support member relative to a remainder of the coupler and consequent movement of the second engagement feature carried by it. It is further contemplated that a combination of such compliance features could be employed.

Regardless of the configuration of the one or more compliance features, tilting of the engagement axis during an engagement sequence allows one portion of the adaptor coupler, specifically one of the input engagement features, to move toward the drive input (e.g., toward the instrument) while another portion either moves toward or remains a constant distance from drive input and/or manipulator interface. This, in turn, can facilitate engagement in a situation where the adaptor coupler is misaligned with the drive input because it allows a first pair of engagement/complementary engagement features that are aligned with one another to move toward one another so as to at least partially engage one another despite the second pair of engagement/complementary engagement features being mis-aligned, as described in greater detail below. This engagement of the first pair of aligned engagement/complementary engagement features causes the second pair of engagement/complementary engagement features to move into alignment with one another as the adaptor coupler continues to rotate, as will be described in greater detail below, thus allowing the second pair of engagement/complementary engagement features to also come into positive mating engagement without "missing" one another. Similarly, the tilting of the engagement axis can facilitate engagement in a situation where the drive input is not parallel to the adaptor coupler, as the tilting of the engagement axis may raise an engagement feature of the adaptor coupler high enough to engage with its corresponding complementary engagement feature.

As noted above, in some embodiments the compliance features comprise one or more tilt features. In some embodiments, the tilt feature is in the form of a protrusion that extends from an output engaging face of the adaptor coupler. The tilt feature is configured to contact a surface of the drive output when the adaptor coupler is engaged with the drive output such that the output engaging face of the adaptor coupler is held spaced apart from the drive output. The tilt feature acts as fulcrum and defines an axis of rotation about which the adaptor coupler can tilt (i.e., pivot). The axis of rotation may be roughly aligned, in some embodiments, with a line extending between the engagement features on the output engaging face of the adaptor coupler. For example, in some embodiments the tilt feature comprises two protrusions arranged on diametrically opposite sides of the adaptor coupler near the engagement features.

As noted above, in some embodiments the compliance features comprise at least one flexible support member that carries an input engagement feature and is flexibly deformable relative to a remainder of the coupler. The flexible support member is elastically flexible along at least one dimension such that a force applied along a given direction (e.g., having a directional component along a line extending between the drive output and the drive input) to the input engagement feature coupled to the flexible support member causes the flexible support member to elastically flex, thus allowing the input engagement feature to move along the given direction. In some embodiments, the flexible support member comprises an arm having a fixed end coupled to an input facing surface of the coupler and a free end opposite from the fixed end, the arm extending between the fixed and free ends along a direction generally parallel to the input facing surface of the coupler. At least a portion of the arm and/or the input facing surface is flexible such that the free end is movable along a given direction substantially perpendicular to the input facing surface via flexing of the flexible portion of the arm and/or input facing surface. The input engagement feature can be located at or near the free end of the arm or somewhere between the free end and the fixed end.

The compliance feature(s) may reduce or eliminate the issues described above related to failure of the adaptor coupler to achieve positive engagement with the drive input of an instrument. Returning to the engagement sequence described above in relation to FIG. 1A, recall that when the engagement feature 11*a* becomes aligned with the engagement feature 31*a*, the aligned engagement feature 11*a* is prevented from moving into the engagement feature 31*a* because the misaligned engagement feature 11*b* is in contact with the surface 34 of the drive input 30. However, in the case of an adaptor coupler with compliance features in accordance with various embodiments, in the same scenario the contact between the drive input and the misaligned engagement feature would cause the input engagement features to move relative to the drive input such that the engagement axis tilts, in turn causing the aligned engagement feature to move toward and into mating engagement with its complementary engagement feature. Thus, due to the tilting of the engagement axis, the aligned engagement feature is able to engage its complementary engagement feature despite the other engagement feature being misaligned with its complementary engagement feature. Note that in the situation illustrated in FIGS. 1A-1D, such tilting of the engagement axis 97 is not possible, as the orientations of the adaptor coupler 10 and the drive input 30 are fixed and there is no other mechanism that would allow for tilting of the engagement axis 97 (see FIG. 1D). Once the mating engagement of the one engagement feature with its complementary engagement feature occurs, additional rotation of the coupler by the drive output causes the adaptor coupler to move relative to the drive output (and the drive input) along its translational degree of freedom of motion until the heretofore misaligned engagement feature is brought into alignment with and engages its complementary engagement feature, as will be described in greater detail below. Thus, due to the tiltability of the engagement axis of the adaptor coupler, positive mating engagement of the engagement and complementary engagement features is achieved notwithstanding an initial misalignment between adaptor coupler and drive input. Various additional embodiments and aspects of adaptor couplers configured to permit tilting of the engagement axis so as to promote positive mating engagement with drive inputs and drive outputs (are described in greater detail below with reference to FIGS. 4-7D.

Figure 4:
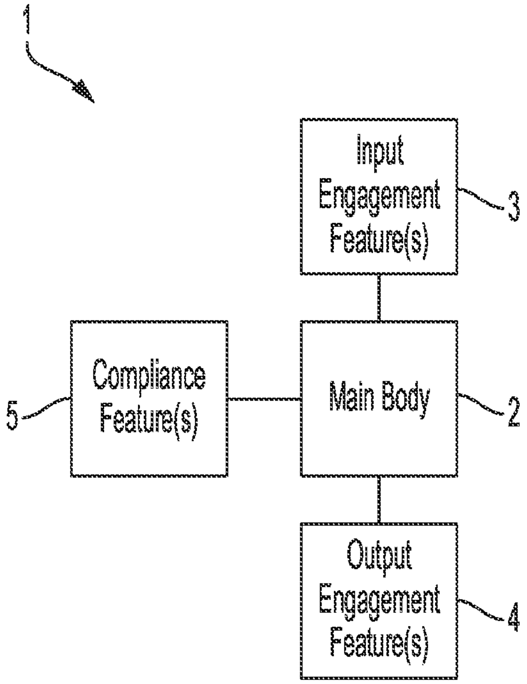
FIG. 4 is a block diagram of an adaptor coupler in accordance with various embodiments.

FIG. 4 depicts a block diagram of an adaptor coupler 1 in accordance with various embodiments. The adaptor coupler 1 comprises a main body portion 2, one or more output engagement features 4, one or more input engagement features 3, and one or more compliance features 5. The output engagement features 4 comprise male or female engagement features configured to matingly engage with complementary female or male engagement features of a drive output (not illustrated). For example, in some embodiments the output engagement features 4 may comprise pins or tabs protruding from an output engaging side of the main body 2. The input engagement features 3 may comprise male or female engagement features configured to matingly engage with complementary female or male engagement features of a drive input of an instrument (not illustrated). For example, in some embodiments the input engagement features 3 may comprise pins or tabs protruding from an input engaging side of the main body 2, which is opposite from the output engaging side of the main body 2. The compliance features 5 are coupled to or are part of the main body 2, the output engagement features 4, and/or the input engagement features 3 and are configured to allow a first input engagement feature 3 to move toward the drive input in a state in which the coupler 1 is engaged with the drive output and a second input engagement feature 3 is in contact with a coupler facing surface of the drive input. In other words, the compliance feature(s) 5 are configured to allow an engagement axis that is tangent to the input engagement features 3 to tilt relative to the drive input in response to contact by the coupler facing surface of the drive input with one of the input engagement features 3. In some embodiments, the compliance features 5 comprises a tilt feature and the tilting of the engagement axis may be caused by tilting of the entire coupler 1 about the tilt feature relative to the drive output and/or drive input. In other embodiments, the compliance features 5 comprises at least one flexible support member coupled to one of the input engagement features 3 and the tilting of the engagement axis may be caused by movement of the input engagement feature 3 coupled to the flexible support member relative to a remainder of the coupler via flexing of the flexible support member. Example embodiments that may be used as the adaptor coupler 1 are described in greater detail below with reference to FIGS. 4-16.

Figure 5A:
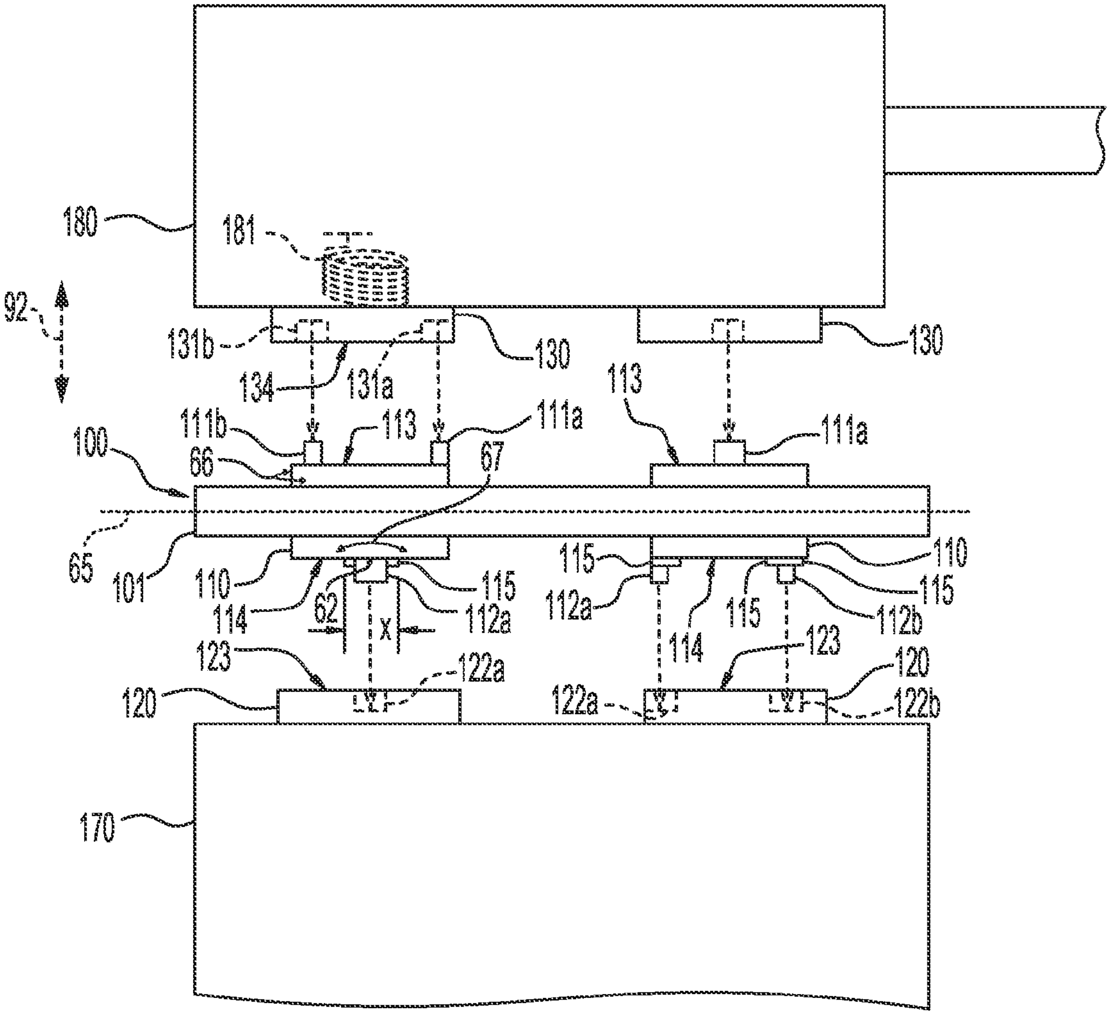
FIG. 5A is a schematic, exploded side view of an embodiment of an instrument adaptor in a mounted state of the instrument adaptor on an interface and a mounted state of an instrument on the instrument adaptor.

FIGS. 5A-8D illustrate an embodiment of an instrument adaptor 100 ("adaptor 100"), which may be used as the adaptor 1 of FIG. 3. In the embodiment of FIGS. 5A-8D, the adaptor coupler comprises tilt features 115, which may be used as the compliance features 5 of FIG. 3. FIG. 5A is a schematic side view of the adaptor 100 in association with a drive output interface 170 to which the adaptor 100 can be mounted and an instrument 180 which can be mounted to the adaptor 100. FIGS. 6A-8D illustrate an adaptor coupler 110 of the adaptor 100, together with a drive output 120 and a drive input 130 in various states: FIGS. 6A-6D correspond to a first state, FIGS. 7A-7D correspond to a second state, and FIGS. 8A-8D correspond to a third state.

As shown in FIG. 5A, the adaptor 100 is configured to be interposed between a drive output interface 170 (e.g., a manipulator interface of a manipulator) and an instrument 180 to couple one or more drive outputs 120 of the drive output interface 170 with one or more drive inputs 130 of the drive input interface of the instrument 180 and to transfer driving forces between the drive outputs 120 and drive inputs 130. In some embodiments, the adaptor 100 is an instrument sterile adaptor (ISA), and thus is also configured to provide a sterile barrier between the interface 170 and the instrument 180, in addition to transferring driving forces. As shown in FIG. 2, the instrument adaptor 100 comprises a frame 101 and one or more adaptor couplers 110, which are described in turn below.

The frame 101 is configured to hold the adaptor couplers 110 at positions that allow the adaptor couplers 110 to couple with the drive outputs 120 of the drive output interface 170 and with the drive inputs 130 of the drive input interface of the instrument 180. In some embodiments, the frame 101 is also configured to removably mount to the drive output interface 170 and/or to removably couple to the instrument 180. In some embodiments, the frame 101 comprises one or more attachment features that allow the frame 101 to be removably attached to the interface 170 and/or instrument 180. In embodiments in which the adaptor 100 is an ISA, the frame 101 also forms part of the sterile barrier between the interface 170 and the instrument 180. In some embodiments, the frame 101 is coupled with a sterile drape (not illustrated but with which those having ordinary skill in the art are familiar) to form a sterile drape assembly.

Figure 5C:
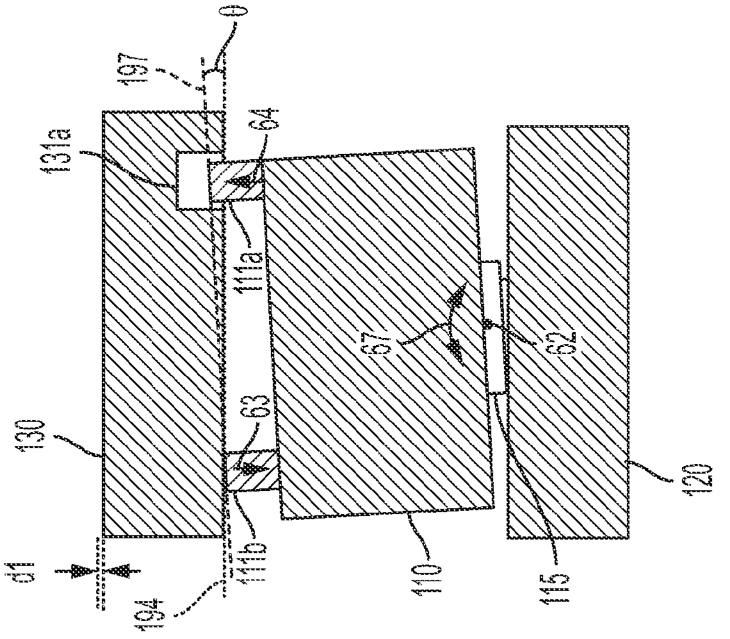
FIG. 5C is a schematic section of the adaptor coupler of FIG. 5B in a second state, with the section taken along a plane extending through a center of the adaptor coupler and parallel to the page in FIG. 5A.
Figure 5B:
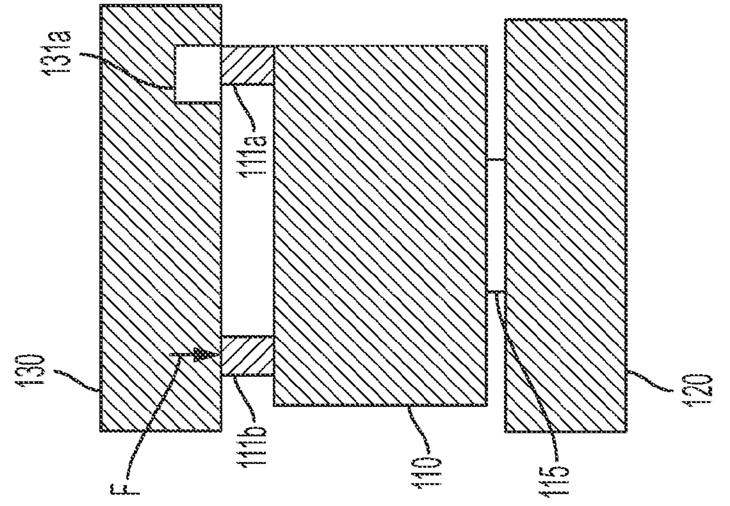
FIG. 5B is a schematic section of an embodiment of an adaptor coupler of the instrument adaptor of FIG. 5A, coupled to a drive output and in a first state while attempting to engage with a drive input, with the section taken along a plane extending through a center of the adaptor coupler and parallel to the page in FIG. 5A.

As noted above, the adaptor 100 comprises one or more adaptor couplers 110. In FIG. 5A, two adaptor couplers 110 are shown, but any number of adaptor couplers 110 equal to or greater than one may be included in the instrument adaptor 100. In general, the number of adaptor couplers should be at least equal to the number of drive outputs and drive inputs that are to be drivingly coupled by the adaptor. The adaptor couplers 110 are rotatably coupled to the frame 101, and each is configured to couple with one of the drive outputs 120 and one of the drive inputs 130. In FIG. 2, the adaptor couplers 110 are shown at two different rotational orientations that are 90 degrees offset from one another to better show different aspects thereof, but in practice the adaptor couplers 110 may have any arbitrary rotational orientations relative to one another. Each adaptor coupler 110 comprises one or more engagement features 111 disposed on a drive input engaging side of the adaptor coupler 110 (i.e., on or in surface 113) and configured to engage with one or more complementary engagement features 131 disposed on a corresponding drive input 130 (i.e., on or in surface 134). Each adaptor coupler 110 also comprises one or more engagement features 112 disposed on a drive output engaging side of the adaptor coupler 110 (i.e., on or in surface 114) and configured to engage with one or more corresponding complementary engagement features 122 disposed on a corresponding drive output 120 (i.e., on or in surface 123). In the embodiment of FIG. 5A-5C there are two engagement features 111*a* and 111*b* arranged to engage with two complementary engagement features 131*a* and 131*b*, respectively, and there are two engagement features 112*a* and 112*b* arranged to engage with two complementary engagement features 122*a* and 122*b*, respectively, but any number of engagement features 111 and 112 may be included in the coupler 110. Also, in the embodiment of FIG. 5A-5C the engagement features 111*a* and 111*b* are disposed diametrically opposite one another on the adaptor coupler and on the surface 113 of the adaptor coupler 110 near an outer periphery thereof. Similarly, the engagement features 112*a* and 112*b* are disposed diametrically opposite one another on the surface 114 of the adaptor coupler 110 and near an outer periphery thereof. Further, the engagement features 111*a* and 111*b* are arranged at angular positions that are approximately 90 degrees offset from the angular positions of the engagement features 112*a* and 112*b*—in other words, a line drawn between the engagement features 111*a* and 111*b* would be approximately perpendicular to a line drawn between the engagement features 112*a* and 112*b*.

The engagement features 111 and 112 may be positioned at any of a variety of positions on their respective sides of the adaptor coupler 110, and they do not necessarily need to be positioned symmetrically at the same relative positions as one another. For example, in FIGS. 5-8D the engagement feature 111*a* is positioned immediately adjacent a periphery (edge) of the adaptor coupler 110 while the engagement feature 111*b* is positioned near to but slightly set back from the periphery of the adaptor coupler 110 (the same is true for the engagement features 112*a* and 112*b*). Such an asymmetrical configuration may provide advantages in some circumstances; for example, an asymmetrical configuration of engagement features 111, 112 such as that shown in FIGS. 5-8D may serve a keying function that allows only certain engagement features to engage one another (e.g., the engagement feature 111*a* will engage only with the complementary engagement feature 131*a* but not with the complementary engagement feature 131*b*). In some embodiments, both engagement features 111 and/or both engagement feature 112 are positioned immediately adjacent the periphery, while in other embodiments both engagement features 111 and/or both engagement features 112 are set back from the periphery. In other embodiments, one or more engagement features 111 or 112 could be positioned radially outward of a main body of the adaptor coupler, for example being positioned on/in a lip or rim that extends radially outward from the adaptor coupler 110. Moreover, the engagement features 111 do not necessarily need to be at diametrically opposite positions as one another. In summary, the number and positions of the engagement features 111 and 112 may be chosen arbitrarily to suit the needs of the system, as long as the engagement features 111 and 112 are capable of mating engagement with the drive output 120 and drive input 130 so as to transfer forces via rotation. However, in some embodiments, it may be beneficial in some circumstances for the engagement features 111 and 112 to be positioned near the periphery to provide for efficient torque transfer and also to allow for increased vertical movement of the engagement features 111 when the adaptor coupler 110 tilts (as described in greater detail below).

As noted above, the engagement features 111 and the complementary engagement features 131, and similarly the engagement features 112 and the complementary engagement features 122 are configured to be matingly engaged with one another. Nonlimiting examples of engagement/complementary engagement features include a variety of male and female features (e.g., pins, tabs, and other similar protrusions for the male features and holes, slots, and other similar recesses for the female features). Another example of engagement/complementary engagement features include pairs of interlocking protrusions, such as intermeshing teeth or interlocking joints.

In FIGS. 5-8D, the engagement features 111 comprise protrusions extending from surface 113 on the drive input engaging side of the coupler 110, the engagement features 112 comprise protrusions extending from surface 114 on the drive output engaging side of the coupler 110, the engagement features 131 comprise recesses into the surface 134 on the drive input 130 configured to receive the engagement features 111, and the engagement features 122 comprise recesses into the surface 123 on the drive output 120 configured to receive the engagement features 112.

The number, relative arrangement, and configuration of engagement features illustrated in FIGS. 5A-5C is not limiting and it should be understood that any arrangement of engagement features 111, 112, 122, and 131 that allows for mating engagement between the coupler 110, the drive output 120, and the drive input 130 can be used. For example, in some embodiments the engagement features 111 and 112 comprise female features while the engagement features 131 and 122 comprise male features. Moreover, it should be understood that the engagement features 111 do not necessarily need to be the same as one another (if multiple engagement features 111 are present), and similarly the engagement features 112 do not necessarily need to be the same as one another (if multiple engagement features 112 are present). For example, in some embodiments, one engagement feature 111 may comprise a male feature and another engagement feature 111 may comprise a female feature. Furthermore, the engagement features 111 do not necessarily need to be the same as the engagement features 112. For example, in some embodiments the engagement features 111 comprise female features while the engagement features 112 comprise male features, while in other embodiments the opposite is the case. Furthermore, in some embodiments the engagement features 111 and/or 112 are arranged at positions on/in the surfaces 13 and 14 different than shown in FIG. 13.

Figure 6A:
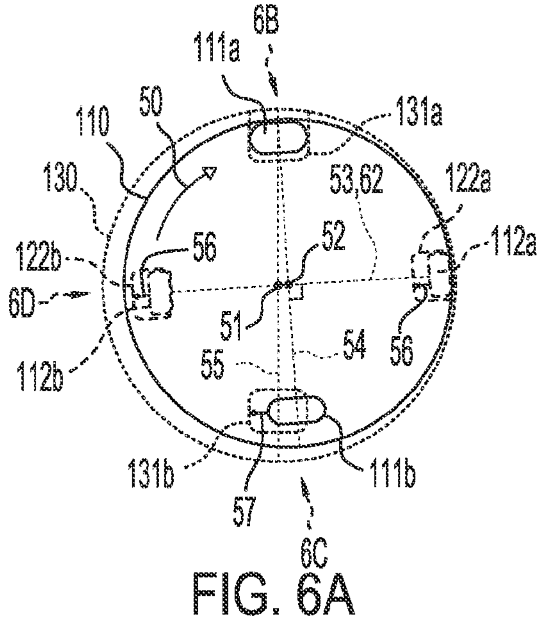
FIG. 6A is a schematic plan view of an embodiment of an adaptor coupler of the instrument adaptor of FIG. 5A, coupled to a drive output in a first state while attempting to engage with a drive input, from the perspective 6A in FIG. 6B.
Figure 6B:
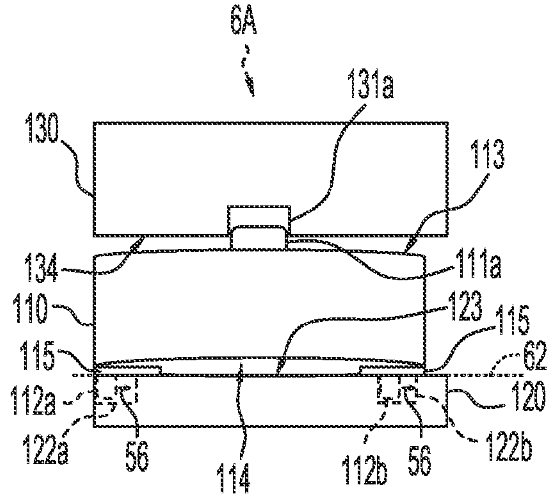
FIG. 6B is a first schematic side view of the adaptor coupler of FIG. 6A in the first state from the perspective 6B in FIG. 6A.
Figure 6C:
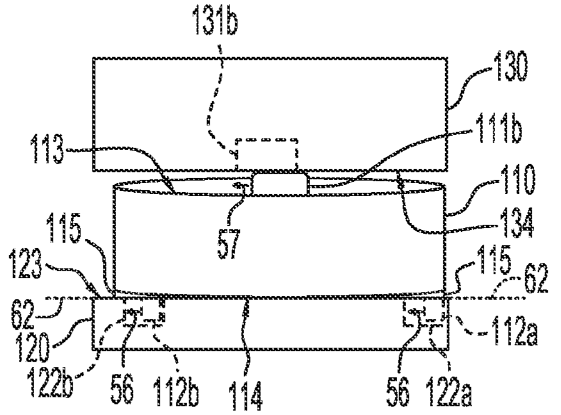
FIG. 6C is a second schematic side view of the adaptor coupler of FIG. 6A in the first state from the perspective 6C in FIG. 6A.
Figure 6D:
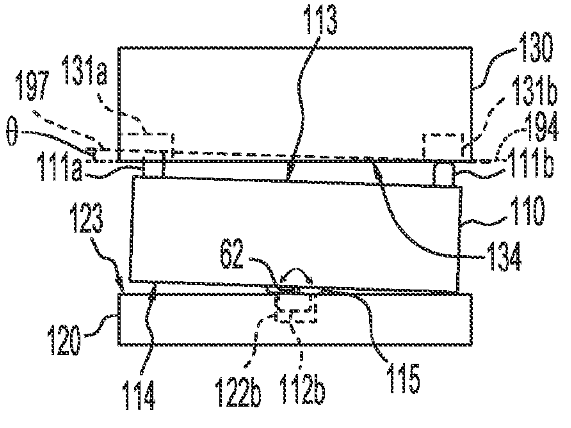
FIG. 6D is a third schematic side view of the adaptor coupler of FIG. 6A in the first state from the perspective 6D in FIG. 6A.

As shown in FIG. 6A, the engagement features 131 are larger than the engagement features 111 in a given dimension. In a manner similar to that described above with reference to FIGS. 1A-2D, this allows for a degree of freedom of motion between the engagement features 111 and the engagement features 131 even after they are brought into mating engagement. Similarly, the engagement features 122 are larger than the engagement features 112 in a given dimension to allow for a degree of freedom of motion after engagement. These degrees of freedom of motion allow the adaptor coupler 110 to move relative to the drive output 120 along an axis 53 and relative to the drive input 130 along an axis 55 after positive engagement of the various engagement features (112/122 and 111/130) is achieved, which allows the adaptor coupler 110 to transfer rotation between the drive output 120 and the drive input 130 even if the drive output 120 and drive input 130 are not perfectly concentrically aligned. In other words, these degrees of freedom of motion allow the adaptor coupler 110 to function similarly to an Oldham coupling.

In some embodiments, tolerances are kept relatively tight along various dimensions other than those mentioned above so as to minimize motion of the adaptor coupler 110 relative to the drive output 120 along directions other than translation along the axis 53 and tilting about axis 62 and to minimize motion of the adaptor coupler 110 relative to the drive input 130 other than translation along the axis 55 and tilting about axis 62. However, in some embodiments the adaptor coupler 110 may retain some additional degrees of freedom of motion relative to the drive output 120 and/or drive input 130 along directions other than those mentioned above, for example due to inevitable finite manufacturing tolerances. Moreover, in some embodiments, motion along additional degrees of freedom of motion relative to the drive output 120 and/or drive input 130 are intentionally designed into the system.

In the embodiment of FIGS. 5-8D, the adaptor couplers 110 are also tiltable relative to the frame 101 of the adaptor 100. More specifically, in embodiments the adaptor couplers 110 are loosely retained within the frame 101 in a manner that allows them to rotate in a plane 65 roughly parallel to the frame 101 (i.e., rotate about an axis roughly perpendicular to plane 65, such as an axis extending through center point 52), as indicated by arrows 66 in FIG. 5, and also to tilt relative to the frame 101, within a limited range of motion, about an axis extending roughly parallel to the plane 65 (e.g., about axis 62). As shown in FIG. 5C, this tilting of the adaptor coupler 110 results in an axis of engagement 197 that is tangent to the input engagement features 111*a* and 111*b* tilting by an angle θ relative to a nominal position for the axis of engagement 197 (which is generally parallel to the coupling faces of drive output 120 and/or drive input 130). Notably, the adaptor couplers 110 are not merely free to tilt just when the adaptor coupler 110 is in a dismounted state, but rather the adaptor couplers 110 also comprise one or more tilt features 115 (described in greater detail below) that are configured to facilitate tilting of the adaptor couplers 110 even in a state in which the adaptor coupler 110 is positively engaged with a drive output 120. More specifically, the tilt features 115 allow the adaptor coupler 110 to tilt relative to the drive output 120 as a result of forces applied to the adaptor coupler 110 by the drive input 130 during an attempted engagement therewith, which tilting facilitates achievement of such engagement as mentioned above and as described in greater detail below.

In contrast, in systems that lack such tilt features, such as the embodiment illustrated in FIGS. 1, 2, and 17, the adaptor couplers 10 may be free to tilt when the adaptor 2100 is in a dismounted state, but are not freely tiltable during an engagement sequence after the adaptor 2100 has been positively engaged with the drive outputs 20 and while engagement is being attempted with the drive input 30. In particular, once mating engagement of the adaptor coupler 10 with the drive output 20 has occurred, the drive output engaging surface 14 of the adaptor coupler 10 makes flush engagement with the surface 23 of the drive output 20 forming a relatively wide and stable base for the adaptor coupler 10, and this flush contact on one side of the adaptor coupler 10 together with the pressure applied by the drive input 30 to the other side of the adaptor coupler 10 prevents tilting of the adaptor couplers 10 relative to the drive output 20 or frame 101. In other words, any forces applied from the drive input 30 to the engagement features 11 of the adaptor coupler 10 are canceled out by equal and opposite reaction forces applied from the surface 23 to the surface 14, resulting in a zero net torque on the adaptor coupler 10 and hence no tilting thereof.

Returning to the tiltable adaptor coupler 110 of FIGS. 5-8B, each tilt feature 115 comprises a protrusion extending from the surface 114 of the adaptor coupler 110. Each tilt feature 115 is configured to contact the surface 123 of the drive output 120 when the engagement features 112 are in mating engagement with the complementary engagement features 122 so as to maintain a slight distance between the surface 114 of the adaptor coupler 110 and the surface 123 of the drive output 120 (when the adaptor coupler 110 is not tilted). The one or more tilt features 115 are arranged so as to allow the adaptor coupler 110 to tilt (rotate) about an axis 62 of rotation (see FIGS. 6A-6D), also referred to herein as a tilt axis 62, with the tilt feature 115 serving as a fulcrum. More specifically, the one or more tilt features 115 form a shelf, step, or mesa-like structure that has at least two portions positioned at diametrically opposite positions on the surface 114, with the structure being relatively narrow along one dimension (indicated by "x" in FIG. 5A) as compared to a width of the main body and surface 114 of the adaptor coupler 110, where the dimension x is transverse to a line extending between the two portions of the shelf-like structure. The shelf-like structure formed by the one or more tilt features 115 may be a single continuous structure, for example as formed by a single tilt feature 115 that extends across nearly the full width of the surface 114, or it may be a discontinuous structure having at least two separate portions formed by multiple tilt features 115 positioned on opposite sides of the adaptor coupler 110 as in the embodiment illustrated in FIGS. 5-8D. Because the shelf-like structure formed by the tilt features 115 is relatively narrow in the dimension x, when the adaptor coupler 110 is engaged with the drive output 120 the coupler 110 will tilt relatively easily about an axis 62 that is roughly perpendicular to the dimension x, as indicated by the arrows 67 (see FIG. 5C). In the illustrated embodiment with two tilt features 115 positioned diametrically opposite from one another, the axis 62 corresponds to a line extending between the two tilt features. In an embodiment with a single tilt feature 115 extending across the surface 114, the axis 62 corresponds to a line extending along a longitudinal dimension of the tilt feature 115. The tilting of the adaptor coupler 110 about the tilt features 115 may occur in response to the application of an unequal vertical forces to the adaptor coupler 110 on opposite sides of the axis 62 (vertical here referring to the up/down orientation illustrated in FIG. 5). For example, if a downward force is applied to the engagement feature 111*a* and none is applied to the engagement feature 111*b*, then a net torque will be generated that causes the adaptor coupler to tilt in the manner shown in FIGS. 6A-6D (explained in greater detail below). In the embodiment of FIGS. 5-8D, the axis 62 of rotation happens to be aligned with the line 53 extending between the engagement features 112 because the tilt features 115 are positioned at the engagement features 112, but in other embodiments this is not necessarily the case.

In some embodiments, the tilt features 115 may have a relatively flat bottom surface that contacts the surface 123 of the drive output 120 in an approximately flush manner. For example, the tilt feature 115 may form a shelf or ledge that rests on the surface 123 on a relatively localized area around the recess of one of the engagement features 122. In other embodiments, the tilt feature 115 may have a bottom surface that is convex to further encourage or facilitate tilting. In other embodiments, the tilt feature 115 may have a bottom surface that has a relatively sharp ridge or apex. In some embodiments, edges of the tilt features 115 may be chamfered or beveled to further facilitate tilting.

Figure 7A:
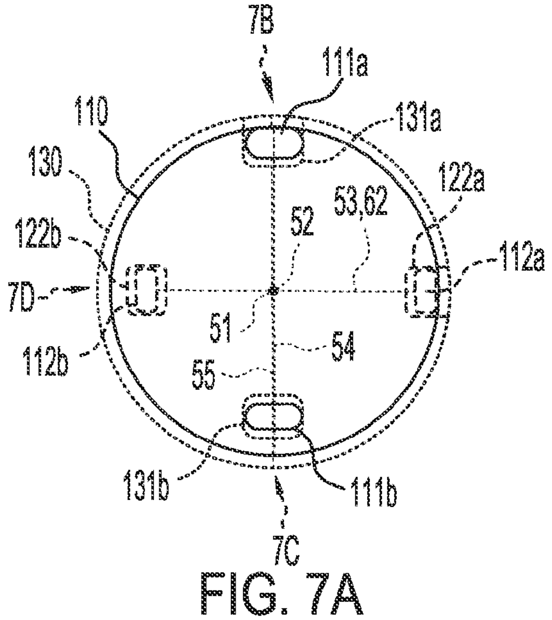
FIG. 7A is a schematic plan view of the adaptor coupler of FIG. 6A in a second state while attempting to engage with the drive input from the perspective 7A in FIG. 7B.
Figure 7B:
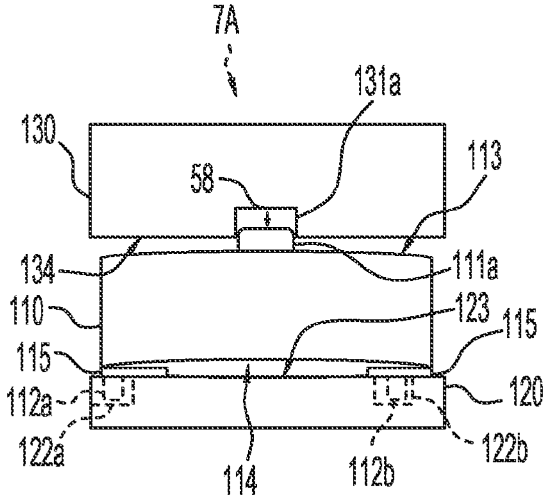
FIG. 7B is a first schematic side view of the adaptor coupler of FIG. 7A in the second state from the perspective 7B in FIG. 7A.
Figure 7C:
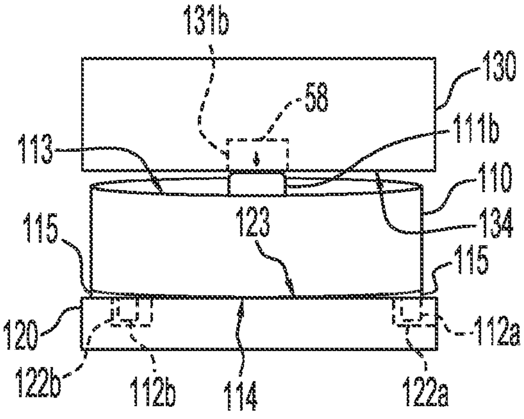
FIG. 7C is a second schematic side view of the adaptor coupler of FIG. 7A in the second state from the perspective 7C in FIG. 7A.
Figure 7D:
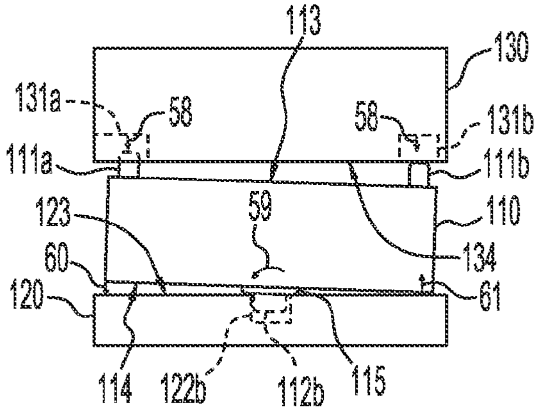
FIG. 7D is a third schematic side view of the adaptor coupler of FIG. 7A in the second state from the perspective 7D in FIG. 7A.
Figure 8A:
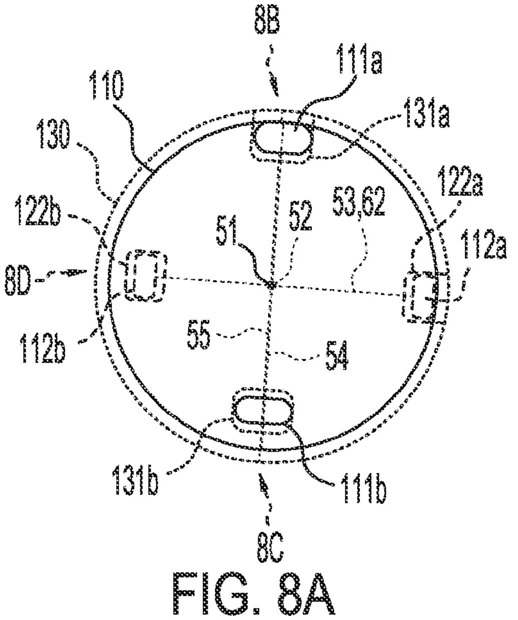
FIG. 8A is a schematic plan view of the adaptor coupler of FIG. 6A in a third state in which the adaptor coupler is fully engaged with the drive input, from the perspective 8A in FIG. 8B.
Figure 8B:
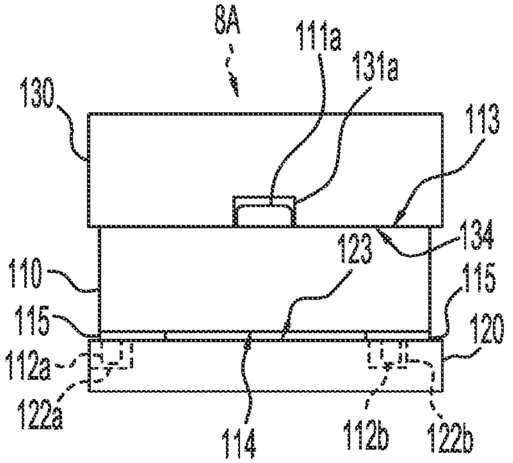
FIG. 8B is a first schematic side view of the adaptor coupler of FIG. 8A in the third state from the perspective 8B in FIG. 8A.
Figure 8C:
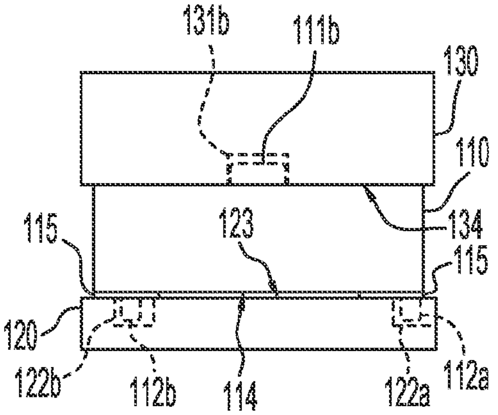
FIG. 8C is a second schematic side view of the adaptor coupler of FIG. 8A in the third state from the perspective 8C in FIG. 8A.
Figure 8D:
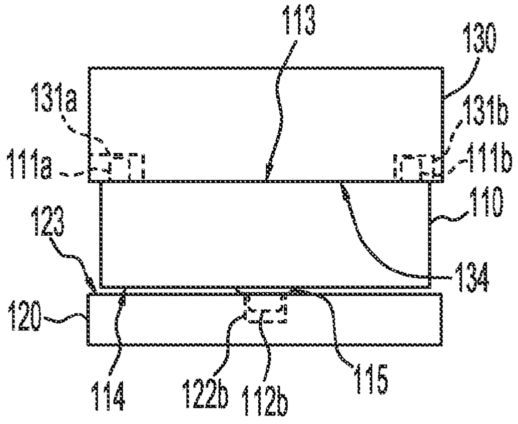
FIG. 8D is a third schematic side view of the adaptor coupler of FIG. 8A in the third state from the perspective 8D in FIG. 8A.

In some embodiments, the one or more tilt features 115 are arranged such that when the adaptor coupler 110 is tilted, the engagement features 111 move in a generally vertical direction (upward or downward) relative to their positions when the adaptor coupler 110 is level (up and down are used here relative to the vertical direction 92 in the orientation shown in FIG. 5A). Although motion of the engagement features is discussed as vertically upward or downward herein, those having ordinary skill in the art would appreciate that as the adaptor coupler 110 is tilted, the engagement features 111 do not necessarily move along a straight line, such as straight up or straight down, but rather their motion may include some horizontal component in addition to a vertical component. For example, in the embodiment illustrated in FIGS. 5-8D the tilt features 115 are disposed on opposite sides of the adaptor coupler 110 at angular positions that are approximately 90 degrees offset relative to the angular positions of the engagement features 111*a* and 111*b*, respectively. In this embodiment, the engagement features 112*a* and 112*b* also are positioned 90 degrees offset from the engagement features 111*a* and 111*b*, respectively, and therefore in this embodiment each of the tilt features 115 is positioned at the same general location as (e.g., fully or partially surrounding) a corresponding engagement feature 112*a* and 112*b*. Because the tilt features 115 are positioned approximately 90 degrees offset from the engagement features 111*a* and 111*b*, the tilt axis 62 of the adaptor coupler 110 is approximately perpendicular to a line 54 extending between the engagement features 111*a* and 111*b*, as shown in FIGS. 6A, 7A, and 8A. The tilt axis 62 is also perpendicular to an axis of rotation of the coupler 110 that extends through the center 52 of the adaptor coupler 10. Therefore, when the adaptor coupler 110 is tilted about the tilt axis 62, the engagement features 111*a* and 111*b* move vertically (upward and downward) in opposite directions as one another as indicated by the arrows 63 and 64 in FIG. 5C (see also FIG. 6D). The motion of the engagement features 111*a* and 11*b* as indicated by the arrows 63 and 64 is illustrated and described relative to a reference frame fixed to the drive output 120, but those having ordinary skill in the art would appreciate the same motion could be described in other ways based on a different choice of reference frame. (Note that in FIGS. 6A, 7A, and 8A the tilt axis 62 is parallel to an axis 53 of translation of the adaptor coupler 110 along a degree of freedom of motion and thus these axes are indicated by the same dashed line in the Figures). The tilt axis 62 is not necessarily fixed in space and may move depending on the state of the adaptor coupler 110.

The ability of the adaptor coupler 110 to tilt when it is in mating engagement with the drive output 120 (i.e., the engagement features 112 are in mating engagement with the complementary engagement features 122) helps prevent the failure of engagement between the adaptor coupler 110 and the drive input 130 described above in relation to FIGS. 1A-2D. In particular, when an instrument is mounted to the adaptor 100, the surface 134 of the drive input 130 and the engagement features 111*a* and 111*b* are pressed together, for example by a biasing device 181 (e.g., spring) that may be included in one or both of the drive output interface 170 and/or in the instrument 180. In FIG. 5 and in the description below, to simplify the description it will be assumed that the biasing device 181 is part of the instrument and arranged to generate forces that urge the drive input 130 downward against the adaptor coupler 110 while the drive output 120 is held stationary, but the same principles apply if other biasing arrangements are used (such as including the biasing device 181 in the drive output interface 170 to press the drive outputs 120 upward while holding the drive inputs 130 stationary). When one of the input engagement features 111*a* or 111*b* is aligned with its corresponding complementary engagement feature 131*a* or 131*b*, the pressing of the drive input 130 and the adaptor coupler 110 towards one another results in a downward force F being applied to the other misaligned engagement feature 111*b* or 111*a*, while no such force is exerted on the aligned engagement feature 111*a* or 111*b*, as shown in FIG. 5B (in FIG. 5B the engagement feature 111*a* that is aligned while the engagement feature 11*b* is misaligned). This application of the force F to one engagement feature 111*a* or 111*b* while no such force is applied to the other engagement feature 111*b* or 111*a* generates a moment that urges the adaptor coupler 110 to tilt about the tilt axis 62 in one direction or the other, as shown in FIG. 5C. When both engagement features 111*a* or 111*b* are simultaneously pressed against by the surface 134 of the drive input 130, such as when both engagement features 111 are misaligned from their respectively corresponding engagement feature 131, no net moment is created (two opposite moments cancel one another out) and the adaptor coupler 110 does not tilt. However, when the adaptor coupler 110 is rotated to an orientation in which one of the engagement features 111 comes into alignment with its corresponding engagement feature 131 while the other engagement feature 111 is not aligned with its corresponding engagement feature 131, then the surface of the drive input 130 ceases to press against the aligned engagement feature 111 while continuing to press against the misaligned engagement features 111, and therefore a non-zero net moment is applied to the adaptor coupler 110, causing the coupler 110 to tilt about the tilt features 115 that are in contact with the surface 123 of the drive output 120. The tilting of the adaptor coupler 110 occurs in a direction that causes the aligned engagement feature 111 to move upward so as to be received at least partially into its corresponding engagement feature 131, as indicated by the arrow 64 in FIG. 5C, while the other mis-aligned engagement feature 111 moves downward as indicated by the arrow 63 in FIG. 5C. This causes the engagement axis 197, which is tangent to the engagement features 111*a* and 111*b*, to tilt by an angle θ, as shown in FIG. 5C. Because one of the engagement features 111 moves downward as a result of the tilting, the drive input 130 also moves downward (or the drive output 120 moves upward, depending on perspective) by a distance d1, as shown in FIG. 5C. Because the aligned engagement feature 111 moves upward while being aligned with its corresponding engagement feature 131, the aligned engagement feature 111 is received at least partially into the engagement feature 131, as shown in FIG. 5C, and thus as the coupler 110 continues to rotate, the aligned engagement feature 111 will catch (collide with) an edge of the corresponding engagement feature 131. This contact between the engagement features 111 and 131 causes the adaptor coupler 110 to move relative to the drive output 120 along its remaining degree of freedom of motion in a manner that brings the other engagement feature 111 into alignment with its engagement feature 131, as described in more detail below.

The above-described principles will now be described in greater detail using an example sequence of events illustrated in FIGS. 6A-8D. In FIGS. 6A-6D a state is illustrated in which the adaptor coupler 110 has been rotated in the direction indicated by the arrow 50 until the engagement feature 111*a* has come into alignment with the engagement feature 131*a*. Because the engagement feature 111*a* is no longer in contact with the surface 134, the downward pressure applied by the drive input 130 on the engagement feature 111*b* generates a net torque on the adaptor coupler 110 that causes the adaptor coupler to tilt about the tilt axis 62, resulting in the adaptor coupler 110 assuming the orientation shown FIGS. 6B-6D in which the engagement feature 111*a* is raised upward and partially received into the recess of the engagement feature 131*a*. Thus, as the adaptor coupler 110 continues to rotate in the direction of the arrow 50, the engagement feature 111*a* comes into contact with an edge/rim of the engagement feature 131*a*.

The contact of the engagement feature 111*a* with the edge of the engagement feature 131*a*, together with the continued rotation of the adaptor coupler 110 in direction 50, generates a net force on the adaptor coupler 110 that urges the adaptor coupler 110 to move relative to the drive output 120 generally along the axis 53. (As noted above, the axis 53 corresponds to a degree of freedom of motion of the adaptor coupler 110.) This results in the engagement features 112 moving as indicated by the arrows 56 in FIGS. 6A-6C. Because the engagement feature 111*a* is engaged with the engagement feature 131*a*, as the adaptor coupler 110 moves along the axis 53 and continues to rotate relative to the drive input 30, this causes the engagement feature 111*b* to move toward the engagement feature 131*b*, as indicated by the arrow 57 in FIGS. 6A and 6C. As a result of this movement of the adaptor coupler 110, the center 52 of the adaptor coupler 110 is brought closer into alignment with the center 51 of the drive input 130 and the engagement feature 111*b* is eventually brought into alignment with the engagement feature 131*b*, as illustrated in FIGS. 7A-7D. Once the engagement feature 111*b* is aligned with the engagement feature 131*b*, the engagement feature 111*b* ceases to contact the surface 134 of the drive input 130 and therefore the force resulting from this contact that previously resisted the downward pressing of the drive input 130 is removed. As a result, the drive input 130 is able to move downward, as indicated by the arrows 58 in FIGS. 7A-7D (or the adaptor coupler 110 is able to move upward, depending on frame of reference). Because of the downward movement of the drive input 130, the engagement feature 111*b* will be received into the engagement feature 131*b*. The drive input 130 will continue to move downward until the surface 134 comes into contact with the surface 113 of the adaptor coupler 110, whereupon the drive input 130 will apply downward pressure on the adaptor coupler 110 that causes it to tilt, as indicated by the arrow 59, back into a level orientation, resulting in the adaptor coupler 110 assuming the orientation illustrated in FIGS. 8A-8D. In the state illustrated in FIGS. 8A-8D, the adaptor coupler 110 is positively engaged with both of the drive output 120 and the drive input 130 by virtue of the mating engagement of the engagement features 111 and 112 with the respective complementary engagement features 122 and 131.

Although the tilt features 115 are disposed at approximately the same locations as the engagement features 112*a* and 112*b* in FIGS. 5-8D, in other embodiments different arrangements could be used. For example, the tilt features 115 could be positioned near, but not necessarily at the same location as, the engagement features 112*a* and 112*b*. As another example, the tilt features 115 could be positioned along the circumference of the adaptor coupler 110 at angular positions that are partway between the engagement features 112*a* and 112*b* and the engagement features 111*a* and 111*b*.

Furthermore, although the one or more tilt features 115 comprise two tilt features 115 in the embodiment of FIGS. 5-8D, in other embodiments different numbers and/or configuration of tilt features 115 can be envisioned based on the disclosure herein. For example, in some embodiments, the one or more tilt features 115 comprises a single tilt feature 115 that extends generally in opposite radial directions across the adaptor coupler 110 along the direction of the tilt axis 62, the length of which can vary. Likewise, a series of shorter length tilt feature segments could be used.

Moreover, although the placement of the tilt features 115 is such that the tilt axis 62 is approximately perpendicular to the line 54 extending between the engagement features 111*a* and 111*b* in the embodiment of FIGS. 5-8D, in other embodiments the placement of the tilt feature(s) may be such that the created tilt axis of the coupler is not perpendicular to the line 54. Generally speaking, the closer that the tilt axis is to being perpendicular to the line 54, the greater the vertical movement that is generated in the engagement features 111*a* and 111*b* as a result of the adaptor coupler 110 being tilted, with essentially no vertical movement occurring when the tilt axis is parallel to the line 54. However, in some embodiments, sufficient vertical movement of the engagement features 111*a* and 111*b* can be obtained even when the tilt axis created by the tilt feature(s) is not perpendicular to the line 54, but is at a non-zero angle.

In addition, although in the embodiment of FIGS. 5-8D the tilt axis 62 runs through a center 52 of the adaptor coupler 110 when viewed from above the adaptor coupler 110 (as in FIGS. 6A, 7A, and 8A), in other embodiments the tilt axis does not run through the center 52.

In the description above, the tilt features 115 were described as protrusions that extend downward from the surface 114 and that contact and rest on the surface 123 of the drive output 120 when the engagement features 112 are engaged with the complementary engagement features 122. However, it should be understood that an adaptor coupler could be provided with other types of tilt features to cause tilting of the adaptor coupler. For example, in some embodiments the engagement features 112 are configured as protrusions having a length that exceeds a depth of the engagement features 122 (configured as recesses) so that, when engaged, the engagement features 112 bottom out in the engagement features 122 and thereby hold the surface 114 a predetermined distance away from the surface 123. In such embodiments, the end portions of the engagement features 112 that contact the bottom of the engagement features 122 constitute tilt features 115 and enable the adaptor coupler 110 to tilt about a tilt axis that extends between the engagement features 112. In either case, the tilt features serve to prevent flush contact between the surfaces 114 and 123, thus allowing relatively easy tilting of the adaptor coupler 110 in response to downward forces applied to the engagement features 111.

FIGS. 9-15 illustrate another embodiment of an instrument adaptor. The instrument adaptor 200 may be used as the instrument adaptor 100 described above. Various parts of the instrument adaptor 200 may be used as corresponding parts of the instrument adaptor 100, and the descriptions above of such parts of the instrument adaptor 100 are applicable to the corresponding parts of the instrument adaptor 200. Duplicative description of aspects of the instrument adaptor 200 that have already been described above in relation to corresponding parts of the instrument adaptor 100 may be omitted below. Corresponding parts of the instrument adaptors 100 and 200 are referred to herein using reference numbers having the same last two digits, such as the adaptor couplers 110 and 210.

Figure 9:
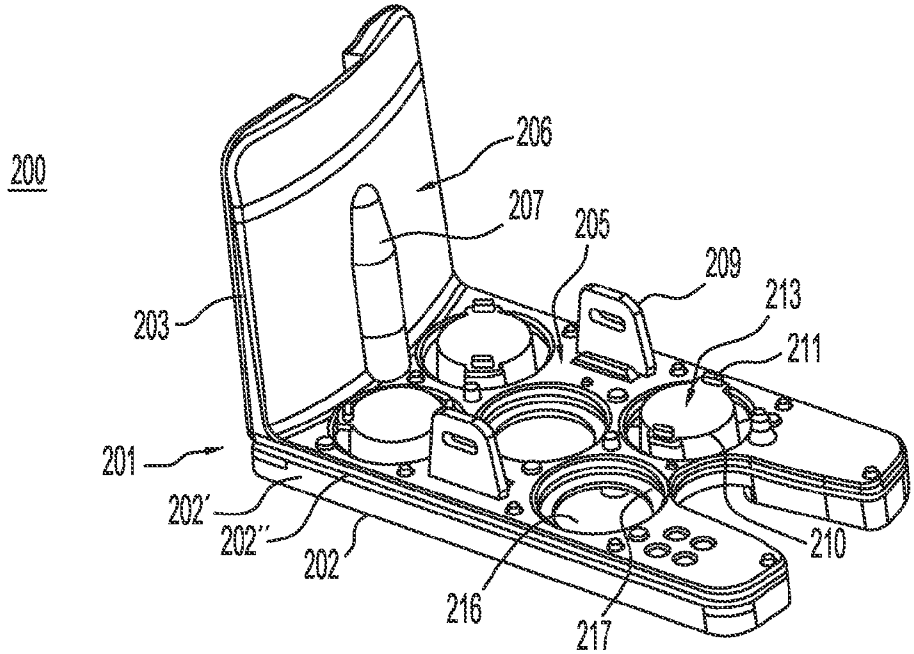
FIG. 9 is perspective view of an embodiment of an instrument adaptor showing an instrument engaging side thereof.
Figure 10:
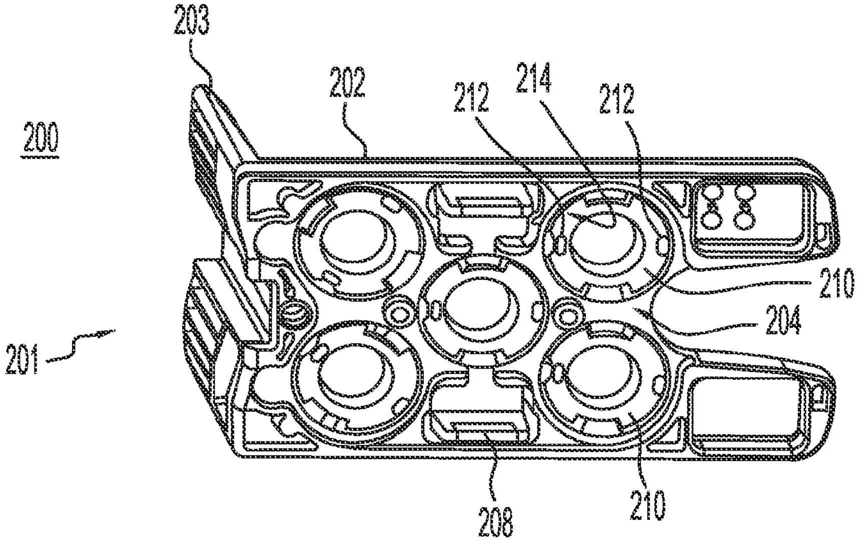
FIG. 10 is perspective view of the instrument adaptor of FIG. 9 showing a manipulator engaging side thereof.

The instrument adaptor 200 is configured as an instrument sterile adaptor ("ISA"), and thus is also referred to herein as an ISA 200. As shown in FIGS. 9 and 10, the ISA 200 comprises a frame 201 and adaptor couplers 210. As shown in FIG. 10, the ISA 200 is configured to be interposed between a manipulator interface 270 and an instrument 280 (such as a medical instrument, for example). More specifically, the frame 201 comprises a first portion 202 and a second portion 203 that are coupled together at approximately a right angle, with the first portion 202 being configured to be disposed between the manipulator interface 270 and the instrument 280, as shown in FIG. 10. The first portion 202 of the frame 201 has a first face 204 (also referred to herein as "manipulator engaging face") configured to mount to the manipulator interface 270 (see FIG. 13) and a second face 205 (also referred to as "instrument engaging face") configured to receive the instrument 280 mounted thereon (see FIG. 14). The first and second faces 204 and 205 are positioned on opposite sides of the frame 201 from one another, which may be referred to as a manipulator engaging side and an instrument engaging side of the frame 201, respectively.

Figure 15:
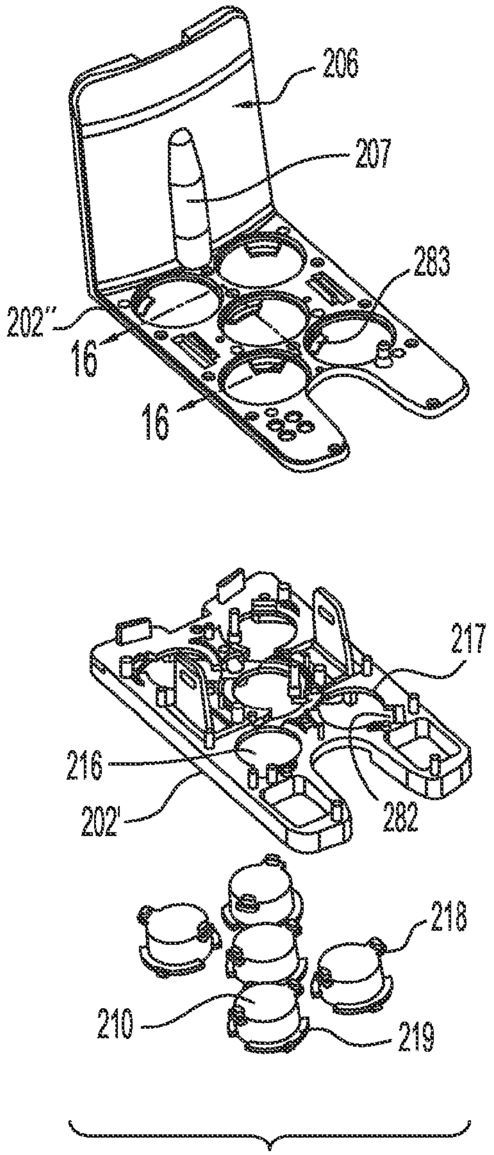
FIG. 15 is an exploded perspective view of the instrument adaptor of FIG. 9.

As shown in FIGS. 9, 10, and 15 the first portion 202 of the frame 201 comprises a number of openings 216, each configured to receive and hold an adaptor coupler 210 therein. In FIG. 9, three openings 216 are shown with adaptor couplers 210 received therein and two of the openings 216 are shown without adaptor couplers 210 to reveal otherwise obscured aspects at the openings 216. As shown in FIGS. 9 and 15, retention features 217 and 283 are disposed around a rim of the opening 216 and are configured to hold the adaptor couplers 210 in the opening 216 while allowing the adaptor coupler 210 to rotate relative to the frame 201, to move vertically relative to the frame 201 (within a limited range of motion), and to tilt relative to the frame 201 (within a limited range or motion).

More specifically, the retention features 217 comprise a lip that extends at least partially around the opening 216, as shown in FIGS. 9 and 15. The retention features 217 are dimensioned so as to interfere with lips 219 extending laterally from on a bottom side of the adaptor coupler 210. Thus, when the adaptor coupler 210 is inserted upward through an opening 216, engagement between the lip 219 and a bottom face of the retention features 217 constrains the adaptor coupler 210 to prevent it from moving further upward through the opening 216 beyond a predetermined position. In addition, the retention features 217 are dimensioned so as to interfere with lips 218 extending laterally from a top side of the adaptor coupler 210. Thus, when the adaptor coupler 216 has been inserted into the opening 216, engagement between the lips 218 and a top face of the retention features 217 constrains the adaptor coupler 210 to prevent it from moving back downward through the opening 216 beyond a predetermined position. In addition, one of more keying features 282 in the form of opening(s) in or between retention features 217 (see FIG. 15) may be provided, with the keying features 282 being arranged to allow the lips 218 to bypass the retention features 217 when aligned with the keying features 282. Thus, the adaptor coupler 210 can be inserted into the opening 216 by aligning the lips 218 and the keying features 282, and then the adaptor coupler 210 can be rotated after the lips 218 have passed through the retention features 217, whereupon the retention features 217 can engage with the bottom face of the lips 218 to constrain the motion of the adaptor coupler 210 and retain the adaptor coupler 210 in the opening 216. Additional retention features 283 may be used to block the keying features 282 to prevent the adaptor coupler 210 from being removed from the opening 216 even if the lips 218 become re-aligned with the keying features 282. For example, as shown in FIG. 15 and as described in greater detail below, the frame 201 may have a multi-layer structure, and the retention features 283 may be disposed in a different layer (i.e., layer 202') than the retention features 217 and keying features 282 (i.e., layer 202"). This may allow for the initial insertion of the adaptor coupler 210 through the layer 202' in the manner described above while the layer 202" is not assembled on the layer 201', followed by rotation of the adaptor coupler 210 such that the lips 218 are not aligned with the keying features 282, followed by assembly of the layer 202" onto the layer 202', which results in the keying feature 282 being blocked by the retention features 283. In other words, the retention features 283 and the retention features 217 cooperate to form a nearly continuous lip or rim around the opening 216 disposed between the lips 218 and 219. For example, as shown in FIG. 16, retention features 283 are opposed by the lips 218 on one side and by the lips 219 on the other side, thus constraining vertical motion of the adaptor coupler relative to the frame 201. In FIG. 16, the retention features 217 are not visible because the section is taken through the region comprising the keying features 282, but in regions where the retention features 217 are present they are positioned similarly to the engagement features 283 and interact with the lips 218 and 219 in a manner similar to the engagement features 283 to constrain the motion of the adaptor coupler 210.

The above-described coupling mechanism results in a relatively loose coupling of the adaptor couplers 210 to the frame 201, with the adaptor couplers 210 retaining multiple degrees of freedom of motion relative to the frame 201. In particular, the adaptor coupler 210 can move vertically within the openings 216 within a limited range of motion indicated by the arrows 2111 in FIG. 16 (e.g., roughly the distance separating the lips 218 and 219), can rotate within and relative to the frame 201 as indicated by the arrows 2113 in FIG. 16, can tilt relative to the frame 201 within a limited range of motion as indicated by the arrows 2112 in FIG. 16, and can translate a small amount side-to-side (i.e., parallel to the instrument engaging face 205) relative to the frame 201 as indicated by the arrows 2114 in FIG. 16.

Figure 11A:
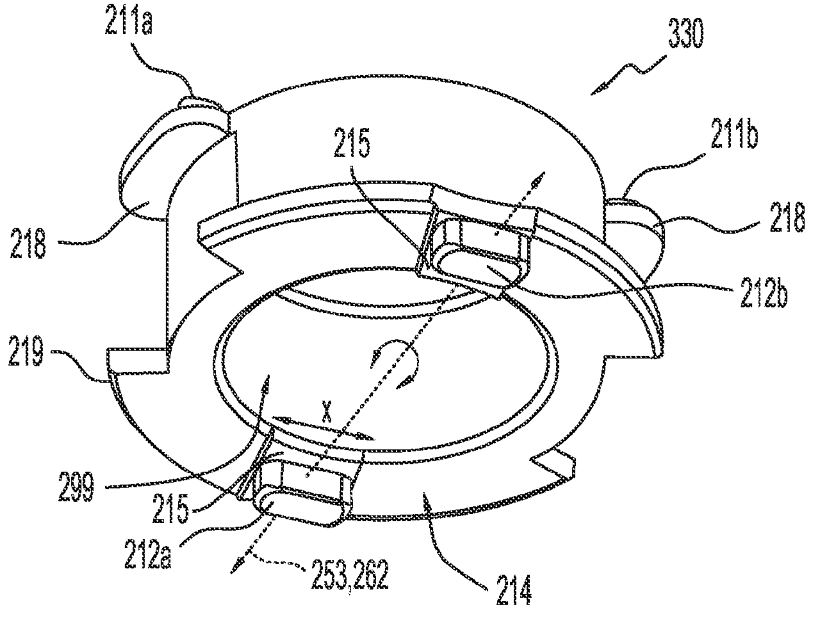
FIG. 11A is perspective view of an adaptor coupler of the instrument adaptor of FIG. 9 showing an output engaging side thereof.

As shown in FIG. 11A, the adaptor coupler 210 comprises engagement features 212*a* and 212*b* protruding downward from a first surface 214 ("bottom surface" or "output engaging surface") on a side of the adaptor coupler 210 that engages the drive outputs (e.g., the top side in the orientation illustrated in FIG. 5), and engagement features 211*a* and 211*b* protruding upward from a second surface 213 ("top surface" or "input engaging surface") on a side of the adaptor coupler 210 that engages the drive inputs (e.g., the bottom side in the orientation illustrated in FIG. 5). Portions of the surface 214 may protrude radially outward to form the lips 219 described above. Similarly, portions of the surface 213 extend radially outward to form the lips 218 described above.

Figure 13:
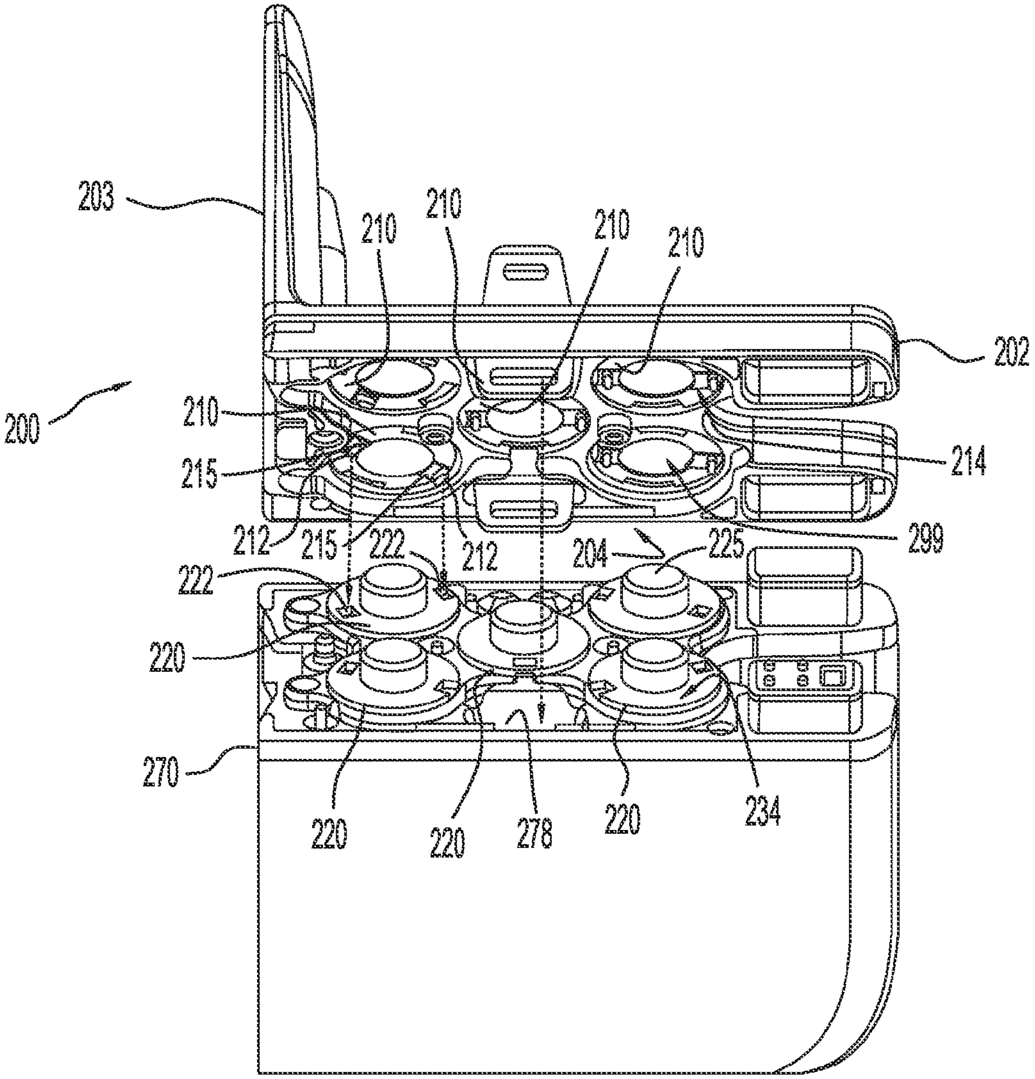
FIG. 13 is an exploded perspective view of the instrument adaptor of FIG. 9 in a mounted state of the instrument adaptor on a manipulator interface.

As shown in FIG. 13, a bottom side of an adaptor coupler 210 (which includes surface 214 and engagement features 212) couples with a top side of a drive output 220 (including surface 234 and engagement features 222) of the manipulator interface 270 when the ISA 200 is mounted to the manipulator interface 270. Upon initial mounting of the ISA 200 to the interface 270, the engagement features 212 of the adaptor couplers 210 may not be engaged with (i.e., received within) their corresponding engagement features 222, but the drive outputs 220 may be rotated in a predetermined manner to cause engagement between the engagement features 212 and 222. The engagement features 222 may be larger than the engagement features 212 along one (lateral) dimension thereof, thus providing the adaptor coupler 210 a degree of freedom of motion to translate relative to the drive output 220 even after the engagement features 212 and 222 are positively engaged. This translational degree of freedom of motion of the adaptor coupler 210 allows for translation along an axis 253 that extends between the engagement features 212*a* and 212*b* (this translational axis 253 is parallel to a tilt axis 262, described further below, and thus these axes are represented by the same dashed line in FIG. 11A). In some embodiments, the engagement between the engagement features 212 and 222 may constrain and substantially prevent relative motion between the adaptor coupler 210 and the drive output 220 along any other degrees of freedom of motion other than the translational and tilting degrees of freedom of motion described herein. In addition, a central raised portion 225 of the drive outputs may be received within a central cavity 299 of the adaptor coupler 210. A fit between the central raised portion 225 and the central cavity 299 may provide some clearance so as to allow the adaptor coupler 210 to move relative to the drive output 220, within a limited range of motion, along the degrees of freedom of motion described herein.

Figure 14:
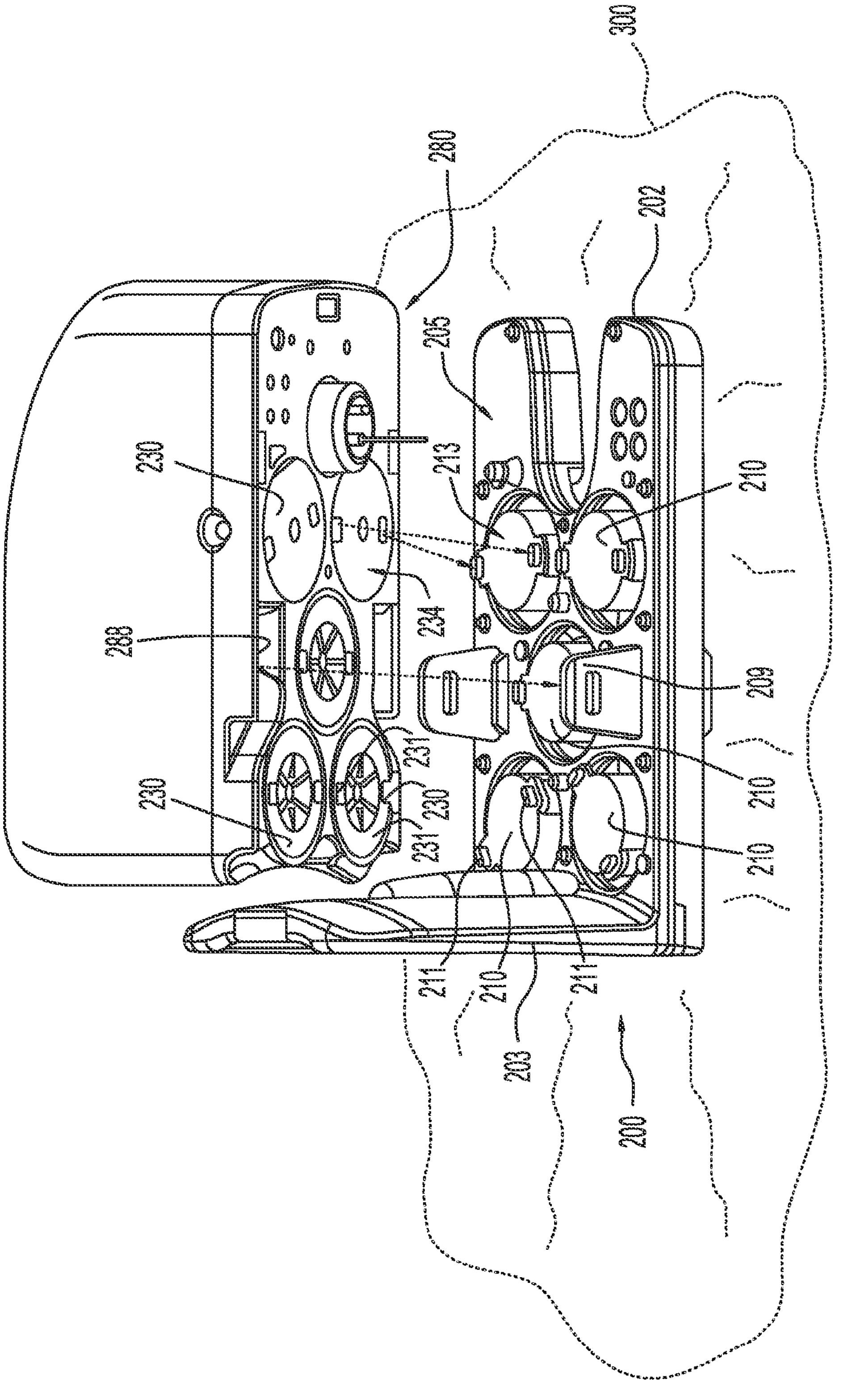
FIG. 14 is an exploded perspective view of the instrument adaptor of FIG. 9 in a mounted state of an instrument on the instrument adaptor.

As shown in FIG. 14, a top side of the adaptor couplers 210 (including surface 213 and engagement features 211) couples with a bottom side of drive inputs 230 (including surface 234 and engagement features 231) of the instrument 280 when the instrument 280 is mounted to the ISA 200. Upon initial mounting of the instrument 280 to the ISA 200, the engagement features 211 of the adaptor couplers 210 may not be engaged with (i.e., received within) their corresponding engagement features 231, but the drive outputs 220 may be rotated in a predetermined manner to cause engagement between the engagement features 211 and 231 in a manner similar to that described above in relation to FIGS. 6A-8D. The engagement features 231 may be larger than the engagement features 211 along one dimension thereof, thus providing the adaptor coupler 210 a degree of freedom of motion to translate relative to the drive input 230 even after the engagement features 211 and 231 are positively engaged. This translational degree of freedom of motion of the adaptor coupler 210 allows for translation relative to the drive input 230 along an axis 244 that extends between the engagement features 211*a* and 211*b*. In some embodiments, the engagement between the engagement features 211 and 231 may constrain and substantially prevent relative motion between the adaptor coupler 210 and the drive input 230 along any other degrees of freedom of motion other than the translational and tilting degrees of freedom of motion described herein.

As shown in FIG. 11A, the adaptor couplers 210 also comprise tilt features 215. The tilt features 215 comprise protrusions downward from the surface 214 at approximately the same location (e.g., locally surrounding) the engagement features 212*a* and 212*b*. The tilt features 215 form a ledge or shelf that is offset vertically from the surface 214 and that hold the surface 214 a distance away from a corresponding surface 223 of a drive output 220 of the manipulator interface 270. The tilt features 215 are relatively narrow in a dimension X perpendicular to the translational axis 253 extending between the engagement features 212, with the tilt features 215 extending less than the full width of the adaptor coupler 210 along this dimension. Thus, when the adaptor coupler is engaged with the drive output 220 of the manipulator interface 270, the tilt features 215 allow the adaptor coupler 210 to tilt relative to the drive output 220 around a tilt axis 262 that extends between the tilt features 215 (parallel to the translational axis 253). More specifically, in vertical projection onto a plane, the edges of the tilt features 215 along the above-noted dimension X are positioned inside of (i.e., closer to the axis 253 than) the engagement features 211, and therefore a downward force applied to one of the engagement features 211 generates a moment on the adaptor coupler 210 that causes the adaptor coupler 210 to tilt about the tilt axis 262.

As noted above, in some embodiments, the first portion 202 of the frame 201 is formed from multiple layers that are sandwiched together. For example, as shown in FIGS. 9 and 15, in some embodiments the first portion 202 comprises two layers 202' and 202" that are joined together. In some embodiments, the layers 202' and 202" are permanently joined together. For example, the layers 202' and 202" may be joined together by heat staking or any other desired joining technique (such as mechanical fasteners, adhesives, friction fittings, welding, etc.). Optionally, in some embodiments, a sterile drape 300 is coupled to the first portion 202, as illustrated schematically in dashed lines in FIG. 14. Specifically, in some embodiments the sterile drape is coupled to the ISA 200 by sandwiching a portion of the drape 300 between the layers 202' and 202" and then joining the layers 202' and 202" with the drape 300 retained therebetween.

Figure 11B:
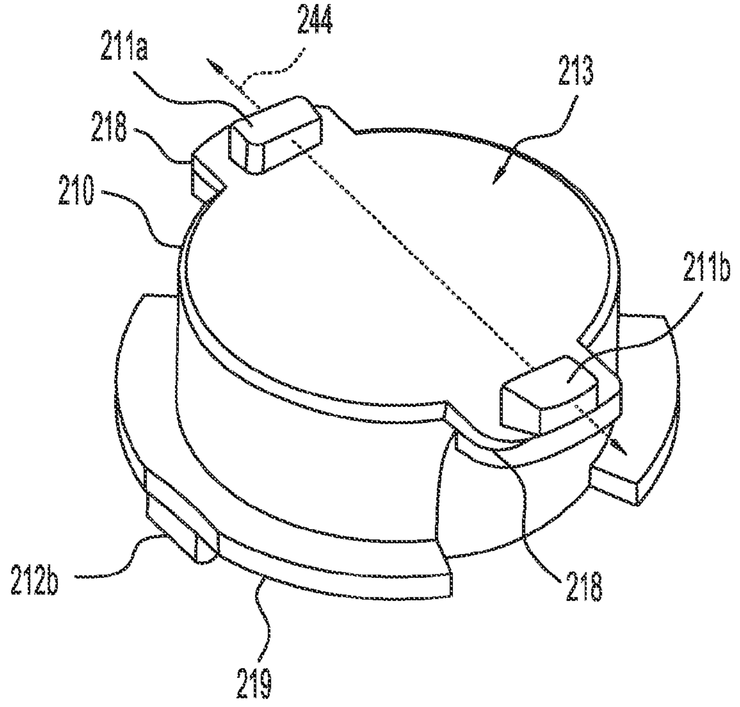
FIG. 11B is perspective view of the adaptor coupler of FIG. 11A showing an input engaging side thereof.
Figure 12:
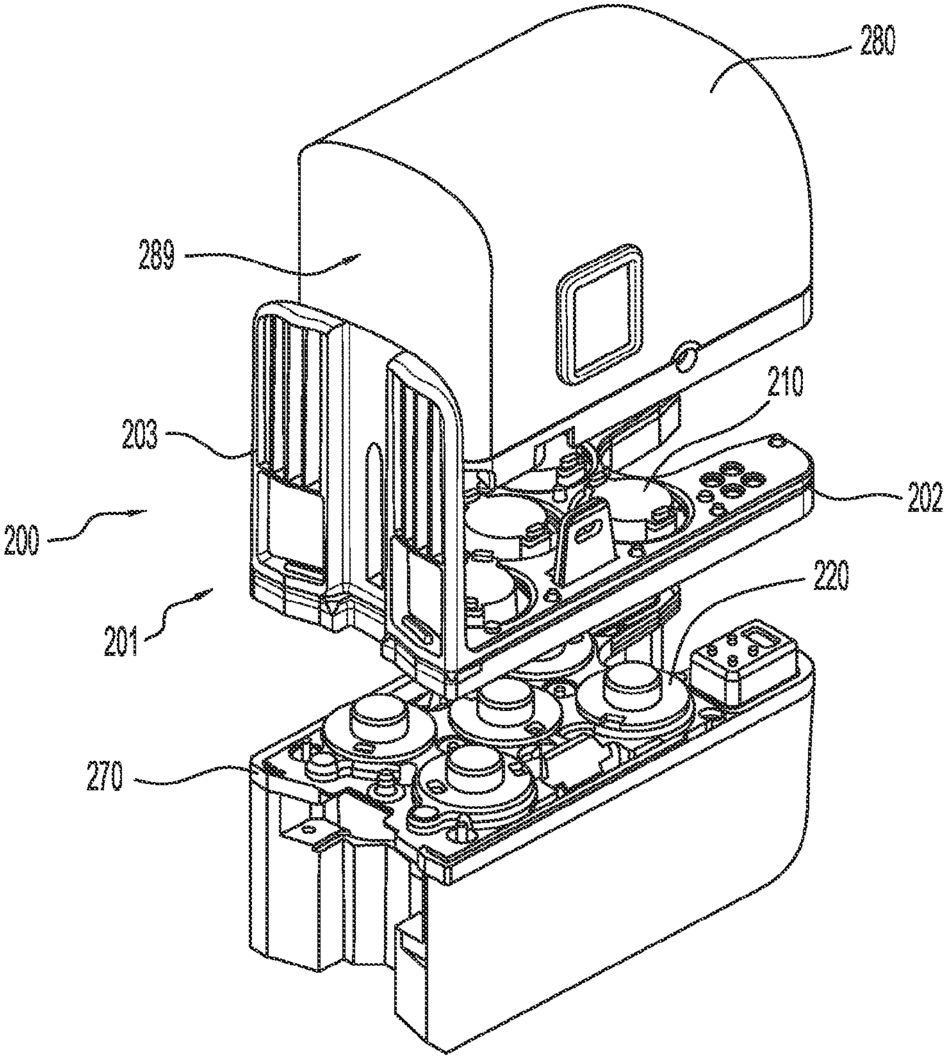
FIG. 12 is an exploded perspective view of the instrument adaptor of FIG. 9 in a mounted state of the instrument adaptor on a manipulator interface and a mounted state of an instrument on the instrument adaptor.

The first portion 202 of the frame 201 also comprises attachment features 208 and 209, as shown in FIGS. 9 and 10. The attachment features 208 are configured to removably attach the ISA 200 to the manipulator interface 270 by engaging complementary attachment features 278, as shown in FIG. 11. The attachment features 209 are configured to removably attach the instrument 280 to the ISA 200 by engaging complementary attachment features 288, as shown in FIG. 14.

As shown in FIGS. 9,10, and 14, the second portion 203 is configured to interface with a portion of the instrument 280 to assist in guiding the instrument 280 into a desired position while mounting the instrument 280 to the ISA 200. In particular, in the embodiment of FIGS. 9-14, the second portion 203 has a convex curved surface 206 (see FIG. 9) that engages with a complementary concave surface 289 of the instrument 280 (see FIG. 12) to constrain motion of the instrument 280. As shown in FIG. 9, the second portion 203 may also include addition alignment features, such as a tapered or bullet shaped alignment feature 207 that progressively further constrains the instrument 280 as the instrument 280 is moved further along the second portion 203 towards the first portion 202.

FIGS. 17A-17D illustrate an embodiment of an adaptor coupler 310, which can be used as the adaptor coupler 1 of FIG. 3. The adaptor coupler 310 may be similar to the adaptor couplers 110 and 210, and thus duplicative description of components of the adaptor coupler 310 that are similar to components already described above will be omitted. The adaptor coupler 310 may be used as part of an adaptor (not illustrated), which is similar to the adaptor 100.

Figure 17A:
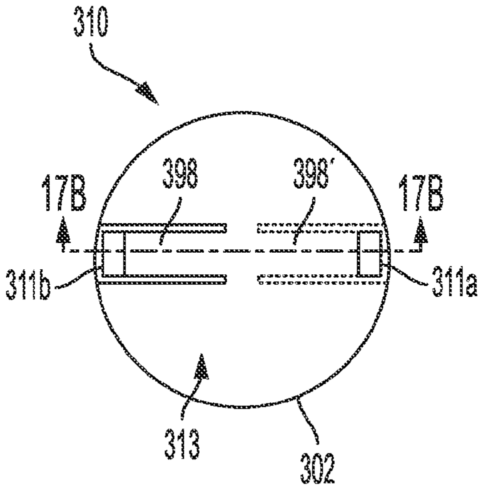
FIG. 17A is a schematic plan view of an embodiment of an adaptor coupler.

The adaptor coupler 310 comprises a main body 302, input engagement features 311 to engage with complementary engagement features 331 of a drive input 330 of an instrument, output engagement features 312 to engage with complementary engagement features (not shown) of a drive output 320, and one or more flexible support members 398, each carrying a respective one of the input engagement features 311. In the embodiments of FIGS. 17A-17E, the flexible support member(s) 398 is/are used as the compliance feature 5 of FIG. 4. In some embodiments only one flexible support member 398 is provided, but in other embodiments multiple flexible support members 398 may be provided. In the embodiment of FIG. 17A, a first flexible support member 398 carrying the engagement feature 311*b* is shown in solid lines and an optional second flexible support member 398' carrying the engagement feature 311*a* is indicated by dashed lines. Below, only one flexible support member 398 is described for convenience but the description thereof is also applicable to additional flexible support members 398 respectively carrying additional input engagement features 311 if present.

Figure 17B:
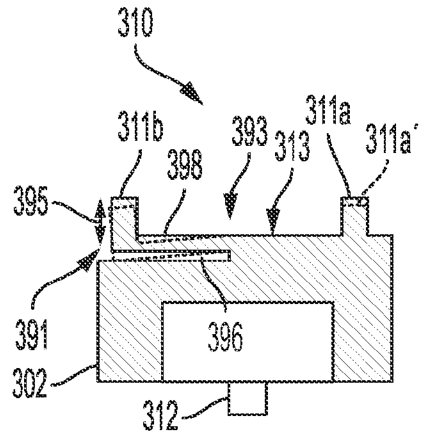
FIG. 17B is a schematic sectional view of the adaptor coupler of FIG. 17A, with the section taken along 17B-17B in FIG. 17A.
Figure 17C:
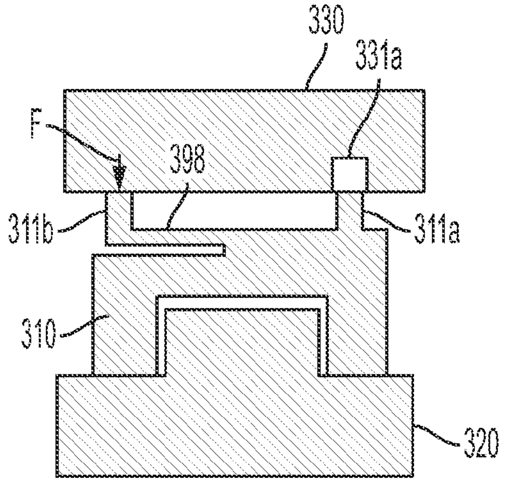
FIG. 17C is a schematic sectional view of the adaptor coupler of FIG. 17A coupled to a drive output and in a first state while attempting to engage with a drive input, with the section taken along 17B-17B in FIG. 17A.
Figure 17D:
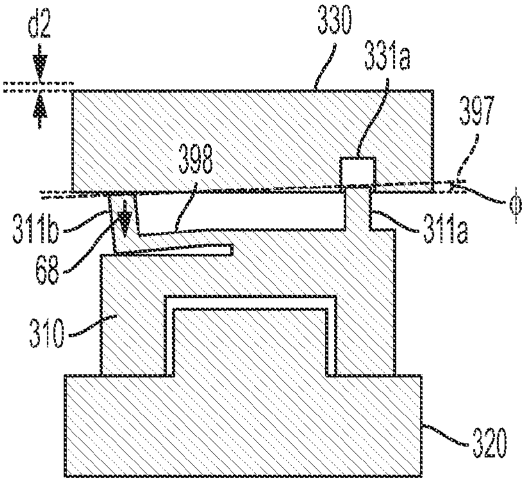
FIG. 17D is a schematic sectional view of the adaptor coupler of FIG. 17A coupled to a drive output and in a second state while attempting to engage with a drive input, with the section taken along 17B-17B in FIG. 17A.

As shown in FIGS. 17A and 17B, the flexible support member 398 comprises an arm having a coupled end 393 attached to the main body 302 and a free end 391 opposite from the coupled end 393. The arm extends between the coupled and free ends roughly parallel to an input facing surface 313 of the coupler 310. In some embodiments, the flexible support member 398 is part of or integrally connected with the input facing surface 313. An open region 396 is provided beneath the flexible support member 398 and at least a portion of the flexible support member 398 is elastically flexible so that the free end 391 of the flexible support member 398 can be moved generally downward and upward into and out of the open region 396 as indicated by the arrows 395 in FIG. 17B, resulting in the flexible support member 398 flexing and moving (for example, in somewhat of a pivoting motion) between a resting position shown by solid lines in FIG. 17B and in FIG. 17C and a flexed position indicated by dotted lines in FIG. 17B and also shown in FIG. 17D. The elastic flexibility of the flexible support member 398 causes the flexible support member 398 to produce a biasing force (e.g., spring force) that resists movement of the flexible support member 398 away from the resting position and also causes the flexible support member 398 to return to the resting position if so moved (once whatever force that moved the flexible support member 398 has been removed).

As noted above, one of the engagement features 311*b* is carried by the flexible support member 398 at or near the free end thereof, as shown in FIGS. 17A-18D. Thus, as the flexible support member 398 is moved between the resting and flexed positions, the engagement features 311*b* moves approximately vertically relative to a remainder of the coupler 310. In particular, when the coupler 310 and the drive input 330 are pressed against one another when one input engagement feature 311*a* is aligned and the other 311*b* is not, this results in a downward force F being applied from the drive input 330 to the misaligned engagement feature 311*b*, as shown in FIG. 17C, and this force F overcomes the biasing force of the flexible support member 398 and causes the engagement feature 311*b* to move downward relative to the remainder of the coupler 310 as indicated by the arrow 68 thus causing the flexible support member 398 to flex (i.e., move from the resting position to the flexed position), as shown in FIG. 17D. This downward movement of the engagement feature 311*b* causes the engagement axis 397 to tilt relative to its nominal position by an angle q as shown in FIG. 17D. Because the engagement feature 311*b* moves downward, this allows the drive input 330 to also move downward by a distance d2, as shown in FIGS. 17C and 17D (the engagement features 311*a* is aligned with the engagement feature 331*a* and thus does not prevent the downward motion of the drive input 330). As a result of this downward motion of the drive input 330, the aligned engagement feature 311*a* moves into (at least partial) engagement with the engagement features 331*a*. Subsequently the continued rotation of the coupler 310 causes engagement of the engagement features 311*b* in a manner similar to that already describe above in relation to the adaptor couplers 110 and 210. Thus, the tilting of the engagement axis 397 caused by the flexing of the flexible support feature 398 allows for the engagement features 311 to positively engage with their complementary engagement features 331 notwithstanding an initial misalignment therebetween.

In embodiments in which only one flexible support feature 398 carrying an input engagement feature 311 is provided, the engagement axis 397 might be tiltable to one side of neutral only. In some circumstances, it may be desired to allow for tilting of the engagement axis 397 to more than one side of neutral. Thus, in some embodiments one or more additional flexible support features 398 are provided to carry the other input engagement features, such as the optional second flexible support feature 398' carrying the input engagement feature 311*a* illustrated in FIG. 17A. The additional flexible support features 398 may be configured similarly to the flexible support feature 398 described above, and they may facilitate tilting of the engagement axis 397 in a manner similar to that described above except that each flexible support feature 398 may allow for tilting toward a different side of neutral.

Figure 17E:
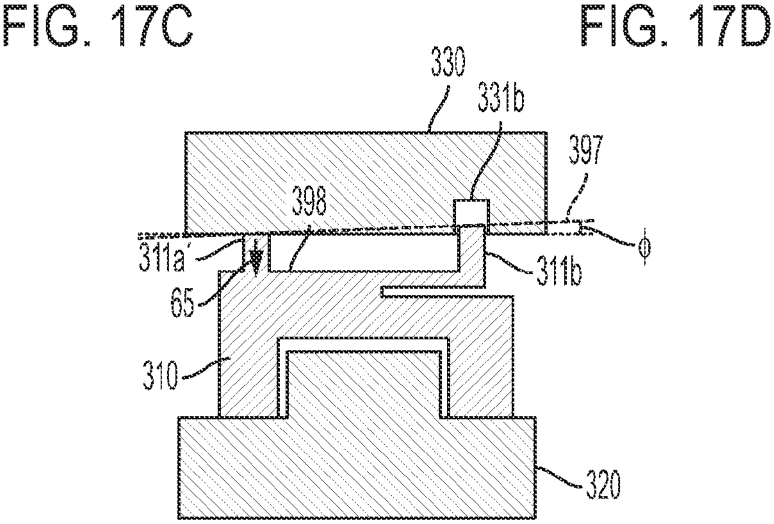

In other embodiments, tilting of the engagement axis 397 in multiple directions can be achieved by configuring the engagement features 311*a* and 311*b* such that the free end of the engagement feature 311*b* carried by the flexible support member 398 is higher than the free end of the other engagement feature 311*a* not carried by a flexible support member in the resting/nominal positions thereof. For example, FIG. 17B illustrates an optional modified engagement feature 311*a'* in dashed lines, which is similar to the engagement feature 311*a* except that it is shorter, and thus the free end of the modified engagement features 311*a'* is lower than the free end of the engagement features 311*b*. The difference in height between the engagement features 311*a* and 311*b* could be obtained in other ways as well, such as by increasing the length of the engagement features 311*b* or configuring the flexible support member 398 to have a resting/nominal position in which the engagement feature 311*b* is raised relative to engagement feature 311*a*. As a result of this difference in heights of the engagement features 311*a* and 311*b*, in a resting state of the adaptor coupler 310 the engagement axis 397 is already tilted in one direction away from being parallel to the coupling faces of drive output 120 and/or drive input 130. Thus, as shown in FIG. 17E, when the lower engagement feature 311*a* is misaligned and the higher engagement feature 311*b* is aligned, the higher engagement feature 311*b* is able to move into engagement with the engagement feature 331*b* due to the tilt of the engagement axis 397. Tilting of the engagement axis 397 in the opposite direction can also occur when the flexible support member 398 is flexed downward, thus lowering the engagement feature 311 carried thereon. For example, when the higher engagement feature 311*b* carried by the flexible support member 398 is out of alignment, the flexible support member 398 flexes downward and causes the engagement axis 397 to tilt, in the same manner as already described above. Thus, tilting of the engagement axis 397 in two directions away from parallel can be achieved.

Those having ordinary skill in the art would appreciate that the description of FIGS. 17A-17E could be reversed with respect to the structures and configurations of engagement features 311*a* and 311*b*, and moreover that other numbers of engagement features and corresponding arrangements of flexible support members, etc. be employed by modification as needed in accordance with the principles of operation described herein.

Figure 18:
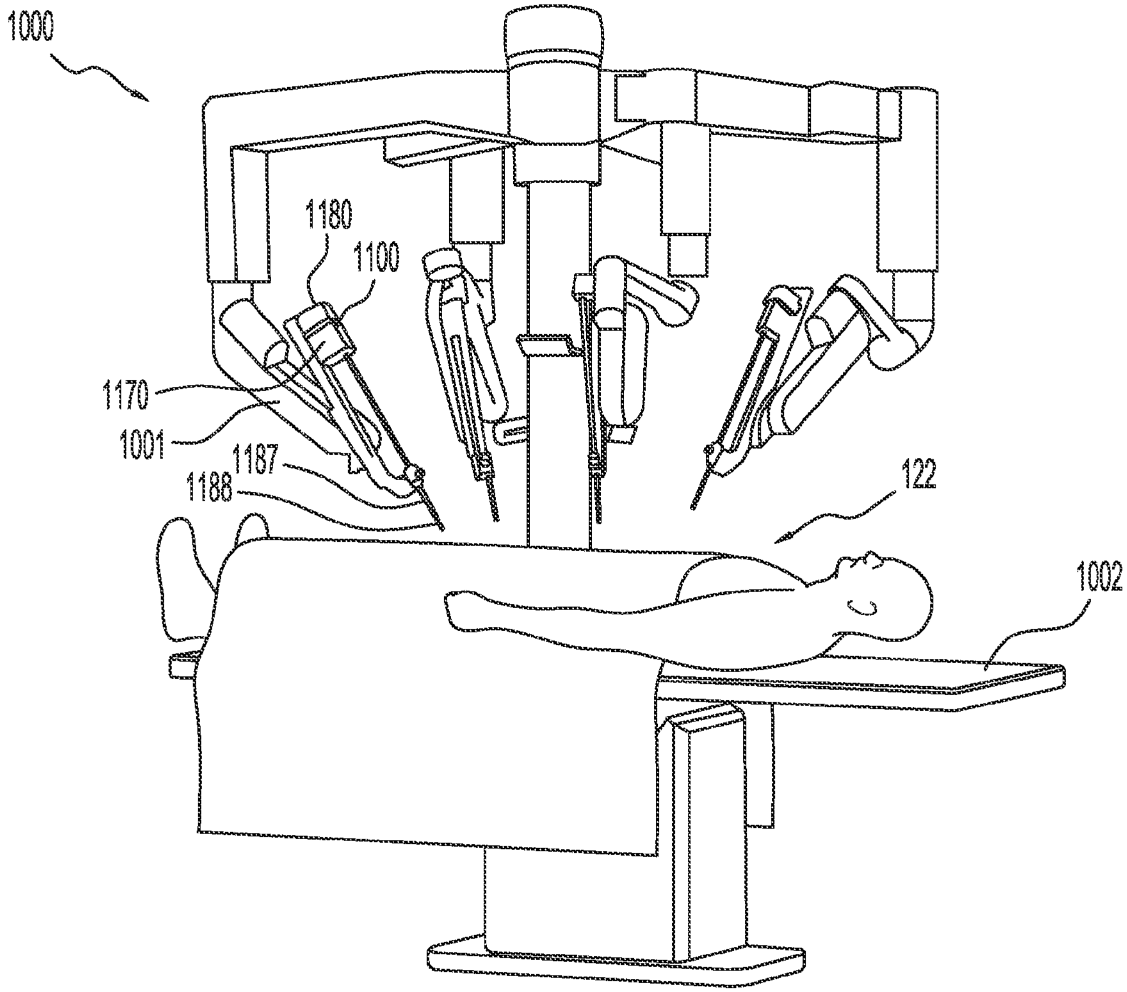
FIG. 18 is a perspective view of an embodiment of a manipulator system.

Turning now to FIG. 18, an example manipulator assembly 1000 will be described. The manipulator assembly 1000 may be part of a computer-assisted manipulator systems (“manipulator systems”), sometimes referred to as robotically assisted systems or robotic systems. The manipulator assembly 1000 may comprise one or more manipulators 1001 that can be operated with the assistance of an electronic controller (e.g., computer) to move and control functions of one or more instruments 1002 when coupled to the manipulators 1001. A manipulator 1001 comprises a plurality of mechanical links connected by joints. An instrument 1180 is removably couplable to (or permanently coupled to) one of the links, typically a distal link of the plural links. In particular, the instrument 1180 is couplable to a manipulator interface 1170 via an instrument sterile adaptor 1100. The joints are operable to cause the links to move (i.e., rotate and/or translate) relative to one another, imparting various degrees of freedom to the manipulator to enable the manipulator 1001 to move the instrument around a worksite. The manipulators 1001 of a manipulator system can be used to transmit a variety of forces and torques to the instruments 1180 to perform various procedures, such as medical procedures or non-medical procedures (e.g., industrial procedures).

The manipulator interface 1170 may be used as one of the interfaces 170 and 270 described above, and comprises drive outputs (similar to the drive outputs 120 or 220) to interface with and mechanically transfer driving forces to corresponding drive inputs (similar to the drive inputs 130 or 230) of the instrument 1180 to control degrees of freedom of motion and/or other functions of the instrument 1180. Electrical power, data signals, vacuum suction, insufflation, irrigation, and/or other useful flows may also be transferred to the instrument 1180 via various interfaces, which may include interfaces of the manipulator 1001 or interfaces of other parts or subsystems to which the instrument 1180 may be operably couplable or coupled (e.g., an auxiliary system). As mentioned above, the manipulator system may be operably coupled (e.g., through a controller) to a console (not illustrated) with user input devices which register user inputs and control operations of the system based on the inputs. In some cases, an input device may be arranged such that as the input device is actuated, the instrument 1180 is controlled to follow or mimic the movement of the input device, which may provide the user a sense of directly controlling the instrument.

The instrument 1180 may be used as one of the instruments 180 and 280 described above. In some embodiments, the instrument is a medical instrument, which may be used to perform medical procedures, such as, for example, surgical, diagnostic, or therapeutic procedures. Medical instruments may include a variety of instruments used to perform medical procedures, such as therapeutic instruments, diagnostic instruments, surgical instruments, and/or imaging instruments. In some examples, the medical instruments may be inserted into a patient through a natural orifice or an incision (including through a port or other guide inserted in the incision). Such instruments that are remotely controlled may be particularly useful, for example, in performing minimally invasive surgical procedures. A minimally invasive surgical procedure may be designed to reduce the amount of tissue that is damaged during a surgical procedure, for example by decreasing the number and/or size of incisions through which medical instruments are inserted. In other embodiments, the instruments 1180 may be non-medical instruments, such as industrial instruments.

The instrument sterile adaptor 1100 may be any one of the instrument adaptors 100 and 200 described above, and may comprise adaptor couplers (similar to the adaptor couplers 110 or 210) that couple the drive outputs of the interface 1170 to the drive inputs of the instrument 1180 in the manner described above in relation to the instrument adaptors 100 and 200. The instrument sterile adaptor 1100 also comprises tilt features, similar to the tilt features 115 or 215, which allow the adaptor couplers to tilt. As shown in FIG. 18, the instrument sterile adaptor 1100 is positioned between the interface 1170 and the instrument 1180 in a mounted configuration.

Herein and in the appended claims, references to a coupler of an adaptor engaging or being engaged with or being in an engaged state with a drive output or a drive input should be understood as meaning that engagement features of the coupler are matingly engaged with corresponding complementary engagement features of the drive output or drive input. For example, with reference to the ISA 200, the adaptor coupler 210 is engaged with a drive output 120 if the engagement features 112 are matingly engaged with the complementary engagement features 122 of the drive output 120, and similarly the adaptor coupler 210 is engaged with a drive input 130 if the engagement features 111 are matingly engaged with the complementary engagement features 131 of the drive input 130.

The embodiments described herein may be well suited for use in any of a variety of medical procedures for which sterility of equipment is desired, as described above. Such procedures could be performed, for example, on human patients, animal patients, human cadavers, animal cadavers, and portions or human or animal anatomy. Medical procedures as contemplated herein include any of those described herein and include, for non-surgical diagnosis, cosmetic procedures, imaging of human or animal anatomy, gathering data from human or animal anatomy, training medical or non-medical personnel, and procedures on tissue removed from human or animal anatomies (without return to the human or animal anatomy). Even if suitable for use in such medical procedures, the embodiments may also be used for benchtop procedures on non-living material and forms that are not part of a human or animal anatomy. Moreover, some embodiments are also suitable for use in non-medical applications, such as industrial robotic uses, and sensing, inspecting, and/or manipulating non-tissue work pieces. In non-limiting embodiments, the techniques, methods, and devices described herein may be used in, or may be part of, a computer-assisted surgical system employing robotic technology such as the da Vinci® Surgical Systems and Ion Endoluminal System commercialized by Intuitive Surgical, Inc., of Sunnyvale, California. Those skilled in the art will understand, however, that aspects disclosed herein may be embodied and implemented in various ways and systems, including manually operated instruments and computer-assisted, teleoperated systems, in both medical and non-medical applications. Reference to the daVinci® Surgical Systems are illustrative and not to be considered as limiting the scope of the disclosure herein.

As used herein and in the claims, terms such as computer-assisted manipulator system, teleoperable manipulator system, or manipulator system, should be understood to refer broadly to any system comprising one or more controllable kinematic structures ("manipulators") comprising one or more links coupled together by one or more joints that can be operated to cause the kinematic structure to move. Such systems may occasionally be referred to in the art and in common usage as robotically assisted systems or robotic systems. The manipulators may have an instrument permanently or removably mounted thereto and may move and operate the instrument. The joints may be driven by drive elements, which may utilize any convenient form of motive power, such as but not limited to electric motors, hydraulic actuators, servomotors, etc. The operation of the manipulator may be controlled by a user (for example through teleoperation), by a computer automatically (so-called autonomous control), or by some combination of these. In examples in which a user controls at least some of the operations of the manipulator, an electronic controller (e.g., a computer) may facilitate or assist in the operation. For example, the electronic controller may "assist" a user-controlled operation by converting control inputs received from the user into electrical signals that actuate drive elements to operate the manipulators, providing feedback to the user, enforcing safety limits, and so on. The term "computer" as used in "computer-assisted manipulator systems" refers broadly to any electronic control device for controlling, or assisting a user in controlling, operations of the manipulator, and is not intended to be limited to things formally defined as or colloquially referred to as "computers." For example, the electronic control device in a computer-assisted manipulator system could range from a traditional "computer" (e.g., a general-purpose processor plus memory storing instructions for the processor to execute) to a low-level dedicated hardware device (analog or digital) such as a discrete logic circuit or application specific integrated circuit (ASIC), or anything in between. Further, manipulator systems may be implemented in a variety of contexts to perform a variety of procedures, both medical and non-medical. Thus, although some examples described in greater detail herein may be focused on a medical context, the devices and principles described herein are also applicable to other contexts, such as industrial manipulator systems.

It is to be understood that both the general description and the detailed description provide example embodiments that are explanatory in nature and are intended to provide an understanding of the present disclosure without limiting the scope of the present disclosure. Various mechanical, compositional, structural, electrical, and operational changes may be made without departing from the spirit and scope of this description and the claims. In some instances, wellknown circuits, structures, and techniques have not been shown or described in detail in order not to obscure the embodiments. Like numbers in two or more figures represent the same or similar elements.

Further, the terminology used herein to describe aspects of the invention, such as spatial and relational terms, is chosen to aid the reader in understanding example embodiments of the invention but is not intended to limit the invention. For example, spatially terms—such as "beneath". "below", "lower", "above", "upper", "proximal", "distal", "up", "down", and the like—may be used herein to describe directions or one element's or feature's spatial relationship to another element or feature as illustrated in the figures. These spatial terms are used relative to the figures and are not limited to a particular reference frame in the real world. Thus, for example, the direction "up" in the figures does not necessarily have to correspond to an "up" in a world reference frame (e.g., away from the Earth's surface). Furthermore, if a different reference frame is considered than the one illustrated in the figures, then the spatial terms used herein may need to be interpreted differently in that different reference frame. For example, the direction referred to as "up" in relation to one of the figures may correspond to a direction that is called "down" in relation to a different reference frame that is rotated 180 degrees from the figure's reference frame. As another example, if a device is turned over 180 degrees in a world reference frame as compared to how it was illustrated in the figures, then an item described herein as being "above" or "over" a second item in relation to the Figures would be "below" or "beneath" the second item in relation to the world reference frame. Thus, the same spatial relationship or direction can be described using different spatial terms depending on which reference frame is being considered. Moreover, the poses of items illustrated in the figure are chosen for convenience of illustration and description, but in an implementation in practice the items may be posed differently.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components, unless specifically noted otherwise. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Unless otherwise noted herein or implied by the context, when terms of approximation such as "substantially," "approximately," "about," "around," "roughly," and the like, are used in conjunction with a stated numerical value, property, or relationship, such as an end-point of a range or geometric properties/relationships (e.g., parallel, perpendicular, straight, etc.), this should be understood as meaning that mathematical exactitude is not required for the value, property, or relationship, and that instead a range of variation is being referred to that includes but is not strictly limited to the stated value, property, or relationship. In particular, the range of variation around the stated value, property, or relationship includes at least any inconsequential variations from the value, property, or relationship, such as variations that are equivalents to the stated value, property, or relationship. The range of variation around the stated value, property, or relationship also includes at least those variations that are typical in the relevant art for the type of item in question due to manufacturing or other tolerances. Furthermore, the range of variation also includes at least variations that are within ±5% of the stated value, property, or relationship. Thus, for example, a line or surface may be considered as being "approximately parallel" to a reference line or surface if any one of the following is true: the smallest angle between the line/surface and the reference is less than or equal to 4.5° (i.e., 5% of) 90°, the angle is less than or equal to manufacturing or other tolerances typical in the art, or the line/surface as constituted is functionally equivalent to the line/surface if it had been perfectly parallel.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. An adaptor for operatively coupling a drive output to a drive input of an instrument, comprising:

a frame comprising a first face configured to mount to a drive output interface and a second face configured to receive an instrument mounted thereon; and a coupler movably coupled to the frame and comprising:

one or more output engagement features configured to engage with a drive output of the drive output interface in a mounted state of the frame to the drive output interface;

input engagement features configured to engage with a drive input of the instrument in a mounted state of the instrument to the frame; and one or more compliance features configured to allow a first input engagement feature of the input engagement features to move toward the drive input in a state in which the coupler is engaged with the drive output and a second input engagement feature of the input engagement features is in contact with a coupler facing surface of the drive input, wherein the one or more compliance features comprise one or both of:

one or more tilt features configured to contact the drive output such that the coupler is tiltable about a tilt axis defined by the tilt features in an engaged state of the coupler with the drive output; and a flexible support member carrying the second input engagement feature and configured to elastically flex relative to a remainder of the coupler such that the second input engagement feature is movable relative to the remainder of the coupler.

2. The adaptor of claim 1, wherein the one or more compliance features are configured to allow an engagement axis tangent to the input engagement features to tilt relative to the drive input, the drive output, or both the drive input and drive output in response to contact by a coupler facing surface of the drive input with the second input engagement feature one of the input engagement features.

3. The adaptor of claim 1, wherein the one or more compliance features comprise the flexible support member.

4. The adaptor of claim 1, wherein the one or more compliance features comprise the one or more tilt features.

5. The adaptor of claim 4, wherein:

the first and second input engagement features are arranged at diametrically opposite positions; and the tilt axis is substantially perpendicular to a line extending between the first and second input engagement features.

6. The adaptor of claim 4, wherein each of the one or more tilt features comprises a protrusion protruding from a first surface on a drive output engaging side of the coupler.

7. The adaptor of claim 6, wherein the one or more tilt features are configured to contact a second surface of the drive output in the engaged state of the coupler to the drive output to prevent the first surface from making flush contact with the second surface.

8. The adaptor of claim 6, wherein each of the one or more tilt features is positioned adjacent to or partially surrounding one of the one or more first output engagement features.

9. The adaptor of claim 4, wherein the one or more tilt features are arranged such that the tilt axis is not aligned with any of the input engagement features.

10. The adaptor of claim 4, wherein the adaptor is an instrument sterile adaptor.

11. The adaptor of claim 4, wherein:

the one or more output engagement features comprise male features protruding from a first surface of the coupler and configured to engage complementary female features in a second surface of the drive output, and each of the one or more tilt features comprises a portion of one of the one or more output engagement features configured to bottom out in the complementary female feature and prevent flush contact between the first surface of the coupler and the second surface of the drive output.

12. The adaptor of claim 4, wherein the one or more output engagement features are configured to engage with one or more first complementary engagement features of the drive output;

wherein the input engagement features are configured to engage with one or more second complementary engagement features of the drive input; and wherein each of the one or more output and input engagement features comprises a male feature and each of the first and second complementary engagement features comprises a female feature.

13. The adaptor of claim 4, wherein the one or more output engagement features are configured to engage with one or more first complementary engagement features of the drive output;

wherein the input engagement features are configured to engage with one or more second complementary engagement features of the drive input wherein each of the one or more output and input engagement features comprises a female feature and each of the first and second complementary engagement features comprises a male feature.

14. The adaptor of claim 4, wherein the drive output interface is part of a manipulator of a computer-assisted manipulator system and the instrument is a medical instrument.

15. The adaptor of claim 4, wherein the coupler has a translational degree of freedom of motion relative to the drive output on condition of the one or more output engagement features being engaged with the drive output.

16. The adaptor of claim 4, wherein the tilt axis is substantially perpendicular to an axis of rotation of the coupler.

17. A sterile drape assembly comprising:

an instrument sterile adaptor comprising:

a frame comprising a first face configured to mount to a drive output interface of equipment and a second face configured to receive an instrument mounted thereon;

a coupler movably coupled to the frame and comprising:

one or more first engagement features configured to engage with a drive output of the drive output interface in a mounted state of the frame to the drive output interface;

one or more second engagement features configured to engage with a drive input of the instrument in a mounted state of the instrument to the frame; and one or more compliance features configured to configured to allow an engagement axis tangent to the second engagement features to tilt relative to the drive input, the drive output, or both the drive input and drive output in response to contact of one of the second engagement features with a coupler facing surface of the drive input in an engaged state of the coupler with the drive output; and a drape coupled to the frame of the instrument sterile adaptor and configured to cover a portion of the equipment wherein the one or more compliance features comprise one or both of:

one or more tilt features configured to contact the drive output such that the coupler is tiltable about a tilt axis defined by the tilt features in an engaged state of the coupler with the drive output; and a flexible support member carrying one of the one or more second engagement features and configured to elastically flex relative to a remainder of the coupler such that the one of the one or more second engagement features is movable relative to the remainder of the coupler.

18. The sterile drape assembly of claim 17, wherein the one or more compliance features comprise the one or more tilt features.

19. The sterile drape assembly of claim 17, wherein the one or more compliance features comprise the flexible support member.

20. A method of using an adaptor to couple a drive output interface to an instrument, comprising:

mounting an adaptor to a drive output interface;

engaging first engagement features of a coupler of the adaptor with a drive output of the drive output interface;

mounting an instrument to the adaptor; and engaging second engagement features of the coupler with a drive input of the instrument by causing an engagement axis of the coupler, which is tangent to the second engagement features, to tilt relative to the drive output while rotating the coupler, the causing the engagement axis to tilt comprising one or both of:

tilting the coupler about a tilt axis via one or more tilt features of the coupler in contact with the drive output; and elastically flexing a flexible support member of the coupler relative to a remainder of the coupler, and, by the flexing, moving one of the second engagement features which is carried by the flexible support member relative to the remainder of the coupler.

* * * * *